United States Patent
Liphardt et al.

(10) Patent No.: US 7,215,424 B1
(45) Date of Patent: *May 8, 2007

(54) BROADBAND ELLIPSOMETER OR POLARIMETER SYSTEM INCLUDING AT LEAST ONE MULTIPLE ELEMENT LENS

(75) Inventors: Martin M. Liphardt, Lincoln, NE (US); Blaine D. Johs, Lincoln, NE (US); Jeffrey S. Hale, Lincoln, NE (US); Craig M. Herzinger, Lincoln, NE (US); Steven E. Green, Lincoln, NE (US); Ping He, Lincoln, NE (US); John A. Woollam, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 171 days.

This patent is subject to a terminal disclaimer.

(21) Appl. No.: 11/103,229

(22) Filed: Apr. 12, 2005

Related U.S. Application Data

(63) Continuation-in-part of application No. 10/925,333, filed on Aug. 24, 2004, and a continuation-in-part of application No. 10/829,620, filed on Apr. 22, 2004, and a continuation-in-part of application No. 10/699,540, filed on Nov. 1, 2003, and a continuation-in-part of application No. 10/050,802, filed on Jan. 15, 2002, now Pat. No. 6,859,278, and a continuation-in-part of application No. 10/034,800, filed on Dec. 28, 2001, now Pat. No. 6,822,738, and a continuation-in-part of application No. 09/583,229, filed on May 30, 2000, now Pat. No. 6,804,004, and a continuation-in-part of application No. 09/419,794, filed on Oct. 18, 1999, now Pat. No. 6,549,282, and a continuation-in-part of application No. 09/162,217, filed on Sep. 29, 1998, now Pat. No. 6,034,777, and a continuation-in-part of application No. 09/144,764, filed on Aug. 31, 1998, now Pat. No. 5,969,818, and a continuation-in-part of application No. 09/033,694, filed on Mar. 3, 1998, now Pat. No. 5,963,327.

(51) Int. Cl.
*G01J 4/00* (2006.01)

(52) U.S. Cl. .................... 356/369; 250/557; 356/364; 356/445; 356/300

(58) Field of Classification Search ........ 356/364–369, 356/338, 336, 327, 33, 328, 630, 448, 445, 356/73, 300; 250/225, 557, 372; 359/793–796, 359/565, 784, 748, 356, 245
See application file for complete search history.

(56) References Cited

U.S. PATENT DOCUMENTS 2,700,918 A    2/1955   Osterberg (Continued)

FOREIGN PATENT DOCUMENTS

| SU | 1518728 | 10/1989 |
|----|---------|---------|
| WO | WO 91/14157 | 9/1991 |
| WO | WO 92/12404 | 7/1992 |
| WO | WO 96/18205 | 6/1996 |
| WO | WO 99/02950 | 1/1999 |

OTHER PUBLICATIONS

EP1 172 642 A2 by Danner et al Japan 2002 2098591 A1 by Danner et al.
Japan 2002 2098591 A1 by Danner et al.

*Primary Examiner*—Gregory J. Toatley, Jr.
*Assistant Examiner*—Tri Ton
(74) *Attorney, Agent, or Firm*—James D. Welch

(57) ABSTRACT

Quasi-achromatic multi-element lens(es) which are precisely mounted with respect to one another in a tubular mounting fixture, and the application thereof in focusing, (and optionally re-colliminating), a spectroscopic electromagnetic beam into a very small, chromatically relatively undispersed, area spot on a material system.

23 Claims, 8 Drawing Sheets

U.S. PATENT DOCUMENTS

| | | | |
|---|---|---|---|
| 3,183,763 A | 5/1965 | Koestes | |
| 4,053,232 A | 10/1977 | Dill et al. | 356/118 |
| 4,105,338 A | 8/1978 | Kuroha | 356/365 |
| 4,210,401 A | 7/1980 | Batten | 356/369 |
| 4,332,476 A | 6/1982 | Stenberg et al. | 356/369 |
| 4,355,903 A | 10/1982 | Sandercock | 356/632 |
| 4,556,292 A | 12/1985 | Mathyssek et al. | 356/487 |
| 4,636,075 A | 1/1987 | Knollenberg | 356/336 |
| 4,647,207 A | 3/1987 | Bjork et al. | 356/369 |
| 4,668,860 A | 5/1987 | Anthon | 250/225 |
| 4,671,657 A | 6/1987 | Calvani et al. | 356/484 |
| 4,750,822 A | 6/1988 | Rosencwaig et al. | 356/445 |
| 4,893,932 A | 1/1990 | Knollenberg | 356/369 |
| 5,042,951 A | 8/1991 | Gold et al. | 356/369 |
| 5,166,752 A | 11/1992 | Spanier et al. | 356/369 |
| 5,329,357 A | 7/1994 | Bernoux et al. | 356/369 |
| 5,333,052 A | 7/1994 | Finarov | 356/369 |
| 5,343,293 A * | 8/1994 | Berger et al. | 356/369 |
| 5,349,471 A | 9/1994 | Morris | 359/565 |
| 5,373,359 A | 12/1994 | Woollam et al. | 356/328 |
| 5,475,525 A | 12/1995 | Tournois et al. | 359/245 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/364 |
| 5,582,646 A | 12/1996 | Woollam | 118/708 |
| 5,596,406 A | 1/1997 | Rosencwaig et al. | 356/327 |
| 5,608,526 A | 3/1997 | Piwonka-Corle et al. | 356/369 |
| 5,666,201 A | 9/1997 | Johs et al. | 356/369 |
| 5,706,212 A | 1/1998 | Thompson et al. | 364/525 |
| 5,757,494 A | 5/1998 | Green et al. | 356/369 |
| 5,793,480 A | 8/1998 | Lacy et al. | 356/73 |
| 5,798,837 A | 8/1998 | Aspnes et al. | 356/369 |
| 5,872,630 A | 2/1999 | Johs et al. | 356/369 |
| 5,877,859 A | 3/1999 | Aspnes | 356/364 |
| 5,917,594 A | 6/1999 | Norton | 356/327 |
| 5,946,098 A | 8/1999 | Johs et al. | 356/364 |
| 5,956,145 A | 9/1999 | Green et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,141,102 A | 10/2000 | Johs et al. | 356/364 |
| 6,268,917 B1 | 7/2001 | Johs | 356/369 |
| 6,587,282 B1 | 7/2003 | Wang et al. | 359/797 |
| 6,804,004 B1 * | 10/2004 | Johs et al. | 356/369 |
| 6,822,738 B1 * | 11/2004 | Johs et al. | 356/369 |
| 6,829,049 B1 | 12/2004 | Uhrich et al. | 356/369 |
| 2002/0024669 A1 | 2/2002 | Danner et al. | |

* cited by examiner

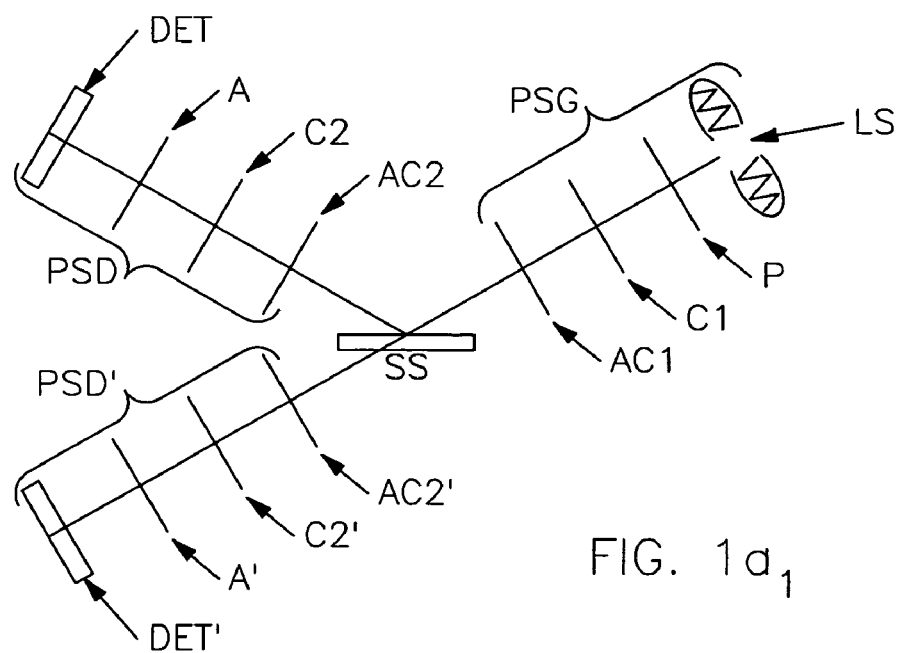
FIG. $1a_1$
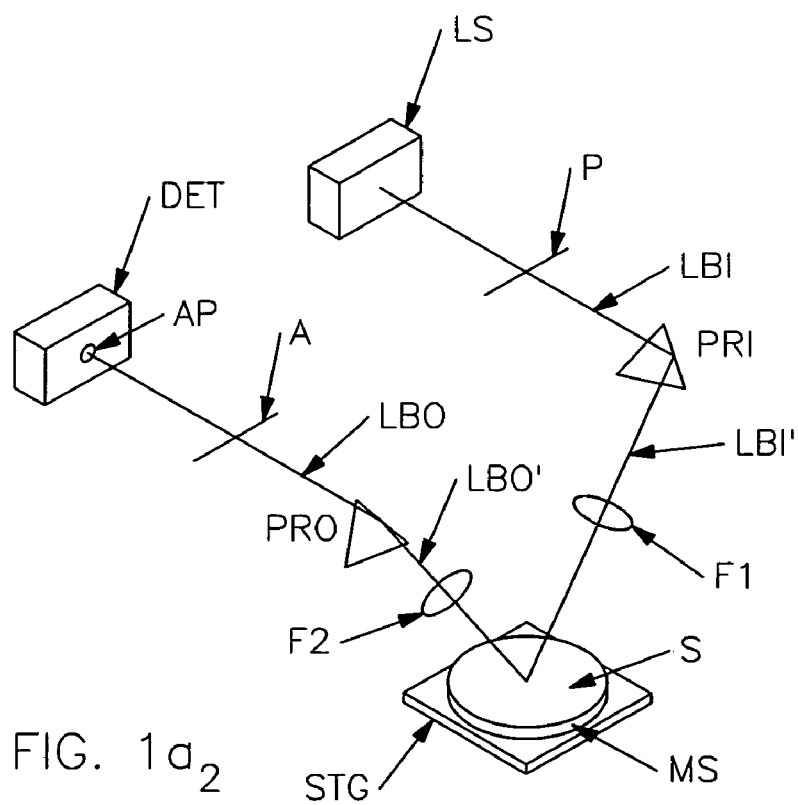
FIG. $1a_2$

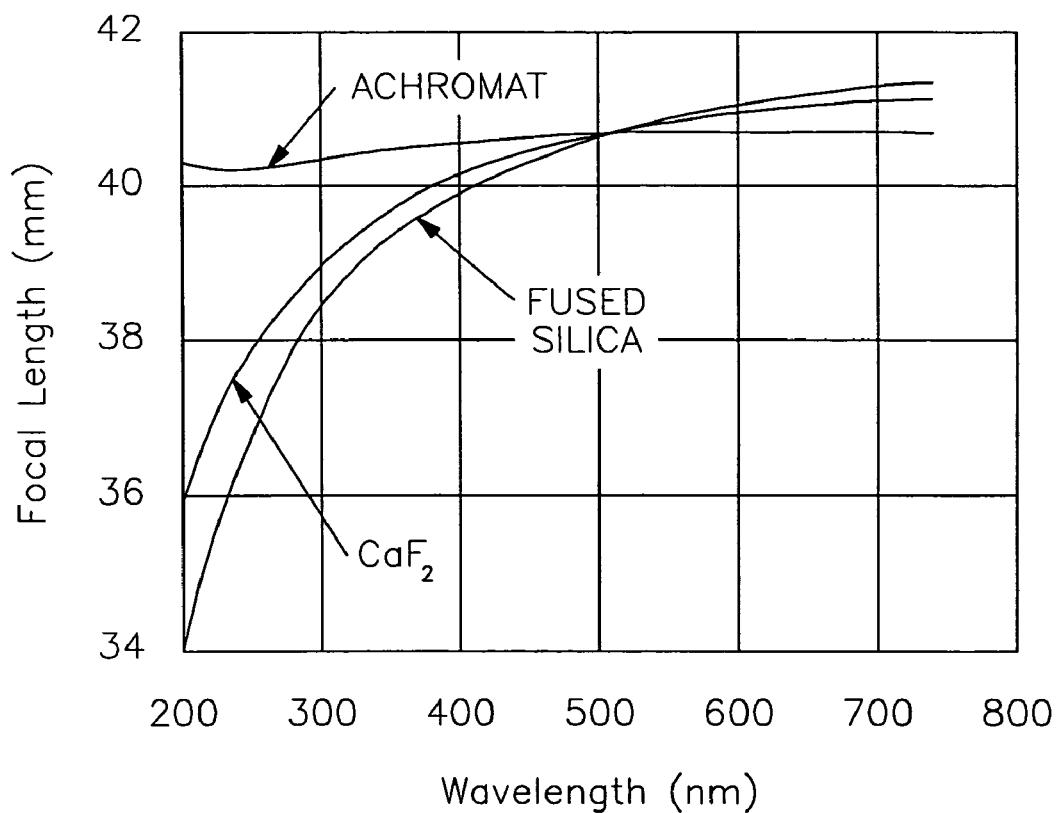
FIG. 1a$_6$
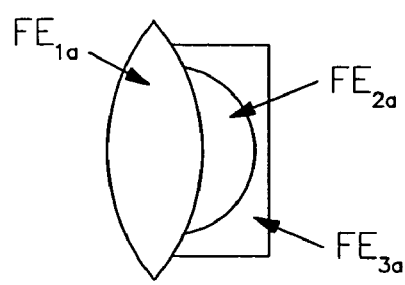
FIG. 1a$_3$

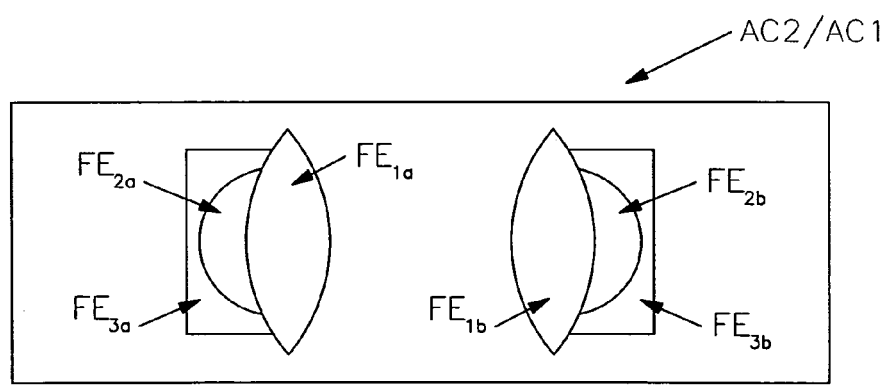
FIG. $1a_4$
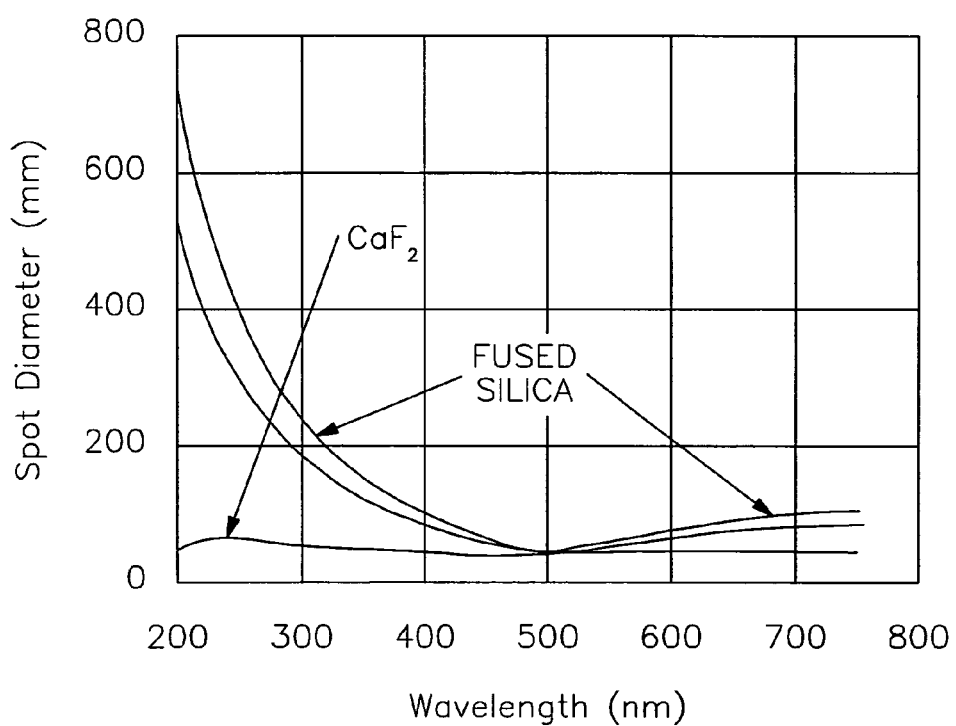
FIG. $1a_5$

FIG. 1a$_7$
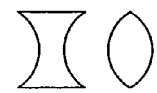
FIG. 1a$_8$
FIG. 1a$_9$
FIG. 1a$_{10}$
FIG. 1a$_{11}$
FIG. 1a$_{12}$
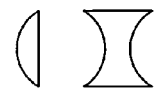
FIG. 1a$_{13}$
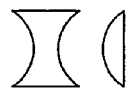
FIG. 1a$_{14}$
FIG. 1a$_{15}$
FIG. 1a$_{16}$
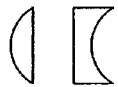
FIG. 1a$_{17}$
FIG. 1a$_{18}$
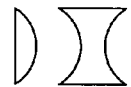
FIG. 1a$_{19}$
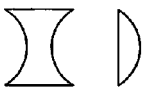
FIG. 1a$_{20}$
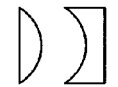
FIG. 1a$_{21}$
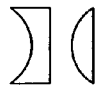
FIG. 1a$_{22}$
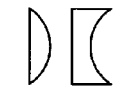
FIG. 1a$_{23}$
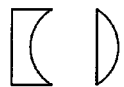
FIG. 1a$_{24}$
C D C D
FIG. 1a$_{25}$
C D D C
FIG. 1a$_{26}$
D C D C
FIG. 1a$_{27}$
D C C D
FIG. 1a$_{28}$

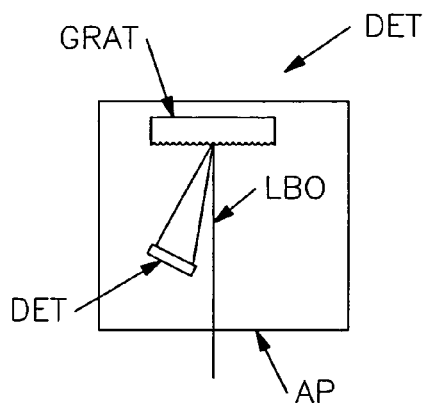
FIG. 1c
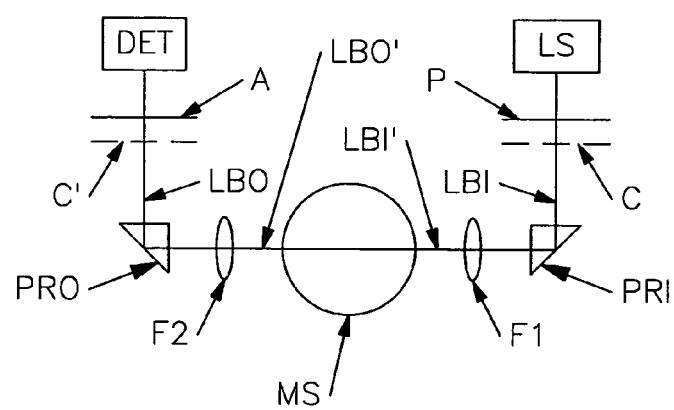
FIG. 2
FIG. 1b₁
FIG. 1b₃
FIG. 1b₂
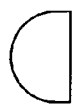
FIG. 1b₄

BROADBAND ELLIPSOMETER OR POLARIMETER SYSTEM INCLUDING AT LEAST ONE MULTIPLE ELEMENT LENS

This application is a Continuation-in-Part of Copending application Ser. No. 10/699,540 Filed Nov. 1, 2003. This application is also a Continuation-in-Part of Co-Pending application Ser. No. 10/829,620 Filed Apr. 22, 2004, and Ser. No. 10/925,333 Filed Aug. 24, 2004, and therevia of Ser. No. 10/034,800, Filed Dec. 28, 2001 (now U.S. Pat. No. 6,822,738) and Ser. No. 10/050,802 Filed Jan. 15, 2002, (now U.S. Pat. No. 6,859,278); and is a CIP of application Ser. No. 09/583,229 Filed May 30, 2000 (now U.S. Pat. No. 6,804,004); and therevia of Ser. No. 09/419,794 Filed Oct. 18, 1999 (now U.S. Pat. No. 6,549,282), and of Ser. No. 09/162,217 Filed Sep. 29, 1998 (now U.S. Pat. No. 6,034,777), and of Ser. No. 09/033,694 Filed Mar. 3, 1998 (now U.S. Pat. No. 5,963,327); and of Ser. No. 09/144,764 Filed Aug. 31, 1998 (now U.S. Pat. No. 5,969,818).

TECHNICAL FIELD

The present invention relates to ellipsometry and polarimetry, and more particularly comprises quasi-achromatic multi-element lens(es) which are precisely mounted with respect to one another in a tubular mounting fixture, and the application thereof in focusing, (and/or colliminating), a spectroscopic electromagnetic beam into a very small, chromatically relatively undispersed, area spot on a material system, said quasi-achromatic multi-element lens(es) providing relatively constant focal length at each wavelength in a large range of wavelengths, including Visible and into the deep UV. Said present invention is further the tubular system, and method of its use in precisely mounting a plurality of lenses with respect to one another therein, as well as a method for breaking correlation between, and evaluating parameters in parameterized equations for calculating retardance entered to, or between, orthogonal components in a beam of spectroscopic electromagnetic radiation by said quasi-achromatic multi-element input and/or output optical elements, (eg. lens(es)), and a typically ellipsometrically indistinguishable, adjacently located, investigated material system with which the spectroscopic beam of electromagnetic radiation is caused to interact.

BACKGROUND

The practice of ellipsometry is well established as a non-destructive approach to determining characteristics of material systems, and can be applied in real time process control. The topic is generally well described in a number of publication, one such publication being a review paper by Collins, titled "Automatic Rotating Element Ellipsometers: Calibration, Operation and Real-Time Applications", Rev. Sci. Instrum, 61(8) (1990).

In general, modern practice of ellipsometry typically involves causing a spectroscopic beam of electromagnetic radiation, in an imposed, known, state of polarization, to interact with a material system at one or more angle(s) of incidence with respect to a normal to a surface thereof, in a plane of incidence. (Note, a plane of incidence contains both a normal to a surface of an investigated material system and the locus of said beam of electromagnetic radiation). Changes in the polarization state of said beam of electromagnetic radiation which occur as a result of said interaction with said material system are indicative of the structure and composition of said material system. The practice of ellipsometry utilizes said changes in polarization state by proposing a mathematical model of the ellipsometer system and the material system investigated by use thereof, obtaining experimental data by application of the ellipsometer system, and applying square error reducing mathematical regression, (typically), to the end that parameters in the mathematical model which characterize the material system are evaluated so that the obtained experimental data, and values calculated by use of the mathematical model have a "best match" relationship.

A typical goal in ellipsometry is to obtain, for each wavelength in, and angle of incidence of said beam of electromagnetic radiation caused to interact with a material system, material system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said material system. Said PSI and DELTA are defined by:

$$\rho = rp/rs = \text{Tan}(\Psi)\exp(i\Delta).$$

As alluded to, the practice of ellipsometry requires that a mathematical model be derived and provided for a material system and for the ellipsometer system being applied. In that light it must be appreciated that an ellipsometer system which is applied to investigate a material system is, generally, sequentially comprised of:

a. a Source of a beam electromagnetic radiation;
b. a Polarizer element;
c. optionally a compensator element;
d. (additional element(s) such as lens(es), beam directing means, and/or windows such as in vacuum chambers);
e. a material system;
f. (additional element(s) such as lens(es), beam directing means, and/or windows such as in vacuum chambers);
g. optionally a compensator element;
h. an Analyzer element; and
i. a Detector System.

Each of said components b.–i. must be accurately represented by a mathematical model of the ellipsometer system along with a vector which represents a beam of electromagnetic radiation provided from said source of a beam electromagnetic radiation, Identified in a. above). (Note that elements (a–d) can be referred to a Polarization State Generator (PSG), and elements (f–i) as a Polarization State Detector (PSD)).

Various ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems.

Where an ellipsometer system is applied to investigate a small region of a material system present, it must be appreciated that the beam of electromagnetic radiation can be convergently entered thereto through an input lens, and, optionally, exit via a re-collimating output lens. It is also possible to have only a collimating lens after the sample. In effect this adds said input, and/or output lens(es) as elements in the ellipsometer system as "additional elements", (eg. identified in d. and f. above), which additional elements must be accounted for in the mathematical model. If this is not done, material system representing parameters determined by application of the ellipsometer system and mathematical regression, will have the effects of said input, (and output), lenses at least partially correlated thereinto, much as if the input and, (output lenses), were integrally a part of the material system.

It is emphasized that where two sequentially adjacent elements in an ellipsometer system are held in a static position with respect to one another while experimental ellipsometric data is acquired, said two sequentially adjacent elements generally appear to be a single element. Hence, a beam directing element adjacent to a lens can appear indistinguishable from said lens as regards the overall effect of said combination of elements. In that light it is to be understood that present input and output lenses are normally structurally fixedly positioned and are not rotatable with respect to a material system present in use, thus preventing breaking correlation between parameters in equations for sequentially adjacent input and output lenses and an investigated material system by an element rotation technique. While correlation of parameters in mathematical equations which describe the effects of groupings of elements, (such as a compensator and an optional element(s)), can be tolerable, correlation between parameters in the mathematical model of an investigated material system and other elements in the ellipsometer system must be broken to allow obtaining accurate material system representing PSI and DELTA values, emphasis added. That is to say that correlation between parameters in equations in a mathematical model which describe the effects of a stationary compensator and a sequentially next located lens element, (eg. correllation between effects of elements c. and d. or between f. and g. identified above), in a beam of electromagnetic radiation might be tolerated to the extent that said correlation does not influence determination of material system describing PSI and DELTA values, but the correlation between parameters in equations which describe the effects of ellipsometer system components (eg. a., b., c., d., f., g., h. and i.), and equations which describe the effects of a present material system (eg. element e. above), absolutely must be broken to allow the ellipsometer system to provide accurate PSI and DELTA values for said material system. Application of ellipsometry to investigation of a material system present can then present a challenge to users of ellipsometer systems in the form of providing a mathematical model for each of an input and output lens, and providing a method by which the effects of said input and output lenses can be separated from the effects of an investigated material system.

One typical approach to overcoming the identified problem, where space considerations are not critical, and where ellipsometer system configuration can be easily modified, is to obtain multiple data sets with an ellipsometer system configured differently during at least two different data set acquisitions. For instance, a data set can be obtained with a material system present and in which a beam of electromagnetic radiation is caused to interact with said material system, and another data set can be obtained with the ellipsometer system configured in a straight-through configuration, where a beam of electromagnetic radiation is caused to pass straight through an ellipsometer system without interacting with a material system. Simultaneous mathematical regression utilizing multiple data sets can allow evaluation of material system characterizing PSI and DELTA values over a range of wavelengths, uncorrelated with present birefringent retardation effects of present input and output lenses. The problem with this approach is that where ellipsometer systems are fit to vacuum chambers for instance, ellipsometer reconfiguration so as to allow acquisition of such multiple data sets can be extremely difficult, if not impossible to carry out.

Another rather obvious solution to the identified problem is to provide input, and output, lenses which are absolutely birefringence-free, and transparent at all electromagnetic beam wavelengths utilized. That is, provide input, and output, lenses which do not attenuate the magnitude of $r_p$ or $r_s$ orthogonal components, (or at least do not change their ratio, $r_p/r_s$), and which also do not enter phase shift between $r_p$ or $r_s$ orthogonal components when said beam of electromagnetic radiation is caused to pass therethrough. While control of the effect of a lens on a ratio, $(r_p/r_s)$, of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc.

As described in Parent application Ser. No. 09/162,217, (which is incorporated herein by reference), controlling stress related change is presently achieved with varying degrees of success, where for instance, windows in a vacuum chamber are subject. Windows provided by BOMCO Inc. are produced with the goal of eliminating birefringence, and are mounted in vacuum chambers using copper gasket seals which help to minimize uneven application of stresses and developed strains thereacross. While some success is achieved via this approach, the BOMCO windows are not "perfect" and do demonstrate some remaining birefringence properties, which can vary in unpredictable ways over a period of usage. In addition, BOMCO windows are expensive, costing on the order of $1000.00 each), and are large in size thereby making adaptation thereof to use in a vacuum chamber difficult at times, particularly in retro-fit scenarios. And, there have been cases where BOMCO windows have broken in use. This is highly undesirable as vacuum chambers are often times caused to contain highly toxic and hazardous materials during, for instance, etching and/or deposition steps required in the fabrication of semiconductor devices. Where vacuum chamber windows are the subject, an alternative to use of the BOMCO windows is to simply use standard vacuum chamber windows, which, while significantly less expensive, demonstrate order of magnitude larger birefringence effects. (Note, BOMCO windows provide birefringent effects on the order of approximately six-tenths (0.6) to two-tenths (0.2) degrees over a range of wavelengths of from four-hundred (400) to seven-hundred-fifty (750) nanometers, whereas standard vacuum windows demonstrate birefringent effects on the order of six (6.0) to three (3.0) degrees over the same range of wavelengths). (Note, birefringent retardation typically follows an approximate inverse wavelength, (eg. 1/wavelength), relationship). However, where standard vacuum chamber windows are utilized, compensation of their effects is required. Similar concerns apply where input and output lenses, and associated ellipsometrically indistinguishable ellipsometer system components are concerned.

A need is thus identified for a method of practicing ellipsometry which enables the breaking of correlation between parameters in equations which describe retardance entered to orthogonal components of a beam of electromagnetic radiation caused to interact with a material system, and parameters in equations which describe birefringent effects on said orthogonal components in said beam of electromagnetic radiation caused by input and output windows of a vacuum chamber, and/or by input and output lenses and/or by electromagnetic beam directing means etc.

Various researchers have previously noted the identified problem, where vacuum chamber windows are the topic, and proposed various first order mathematical model equation correction techniques as solution, which approaches have met with various degrees of success where vacuum chamber input and output windows demonstrate on the order of a maximum of two (2) degrees of birefringence. This, however, leaves the problem unsolved where birefringence approaches six (6.0) degrees, as commonly occurs in standard vacuum chamber windows, and can also occur in lens systems, particularly at wavelengths of four-hundred (400) nanometers and below. Thus is identified a problem to which the present invention calibration methodology applies.

Patents and/or Published Applications which describe the use of multiple element lenses in Ellipsometer and the like systems include:

Applications of Danner et al.:
  EP1 172 642 A2;
  JAPAN 2002 2098591 A
  U.S. 2002/0024669;

Applications:
  WO 91/14157;
  WO 92/12404 by Rudolf Corp.;
  WO 96/18205;
  WO 99/02950;

Patents:
  U.S. Pat. No. 4,671,657 to Calvani et al.;
  U.S. Pat. No. 5,166,752 to Spanier et al.;
  U.S. Pat. No. 5,349,497 to Morris;
  U.S. Pat. No. 5,877,859;
  U.S. Pat. No. 5,963,327 to He et al.;
  U.S. Pat. No. 5,978,087 to Patterson et al.
  Japanese Application H6 (1994)-22332.

Other patents of which the Inventor is aware include those to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to ellipsometer systems.

Additional Patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said patents describes the presence of a variable, transmissive, bi-refringent component which is added, and the application thereof during data acquisition to enable the identified capability.

A patent to Thompson et al. U.S. Pat. No. 5,706,212 teaches a mathematical regression based double fourier series ellipsometer calibration procedure for application, primarily, in calibrating ellipsometers system utilized in infrared wavelength range. Birefringent window-like compensators are described as present in the system thereof, and discussion of correlation of retardations entered by sequentially adjacent elements which do not rotate with respect to one another during data acquisition is described therein.

A patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to Rotating Analyzer ellipsometer systems. The 359 Patent describes a Rotating Analyzer Ellipsometer (RAE) which can comprise a Collimating Lens prior to the Sample being investigated, but has no Lens after said Sample. While not specifically disclosing a focusing lens before the Sample and no collimating lens thereafter, said 359 Patent does obviate the use of a lens before a sample in an ellipsometer, with no lens after said sample being present.

Patents identified in a Search specifically focused on the use of lenses, preferably achromatic, in ellipsometry and related systems are:
  U.S. Pat. Nos. 5,877,859 and 5,798,837 to Aspnes et al.;
  U.S. Pat. No. 5,333,052 to Finarov;
  U.S. Pat. No. 5,608,526 to Piwonka-Corle et al.;
  U.S. Pat. No. 5,793,480 to Lacy et al.;
  U.S. Pat. Nos. 4,636,075 and 4,893,932 to Knollenberg; and
  U.S. Pat. No. 4,668,860 to Anthon.

The most relevant patent found is U.S. Pat. No. 5,917,594 to Norton. However, the system disclosed therein utilizes a spherical mirror to focus an electromagnetic beam onto the surface of a sample in the form of a small spot. Said system further develops both reflection and transmission signals via application of reflective means and of reflection and transmission detectors. The somewhat relevant aspect of the 594 Patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferably zero. It is noted that, as described elsewhere in this Specification, said 594 Patent lens structure, positioning in the 594 Patent system, and purpose thereof are quite distinct from the present invention lens structure and application to focus a beam of electromagnetic radiation. In particular, note that the 594 Patent lens is not applied to directly focus and/or recollimate a beam of electromagnetic radiation onto a sample system, as do the lenses in the present invention. And, while the present invention could utilize a meniscus lens in an embodiment thereof, the 594 Patent specifically requires and employs a negative meniscus lens to correct for spherical aberations caused by off-axis reflection from a spherical mirror, in combination with a positive lens to correct for achromatic aberation introduced by said negative meniscus lens. Further, the present invention system does not require reflection means be present in the path of an electromagnetic beam after its passage through the focusing lens thereof and prior to interacting with a sample system, as does the system in the 594 patent wherein a focusing spherical mirror is functionally required.

A patent to He et al., U.S. Pat. No. 5,963,327 is disclosed as it describes an ellipsometer system which enables providing a polarized beam of electromagnetic radiation at an oblique angle-of-incidence to a sample system in a small spot area.

A patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this application, which patents Claim various Compensator Designs recited in Claims herein, and which patents are incorporated hereinto by reference are:
U.S. Pat. No. 5,946,098 to Johs et al.;
U.S. Pat. No. 5,963,325 to Johs et al.;
U.S. Pat. No. 6,084,674 to Johs et al.;
U.S. Pat. No. 6,084,675 to Herzinger et al.;
U.S. Pat. No. 6,100,981 to Johs et al.;
U.S. Pat. No. 6,118,537 to Johs et al.;
U.S. Pat. No. 6,141,102 to Johs et al.

Patents cited in examination of said patents included U.S. Pat. No. 4,556,292 to Mathyssek et al. and U.S. Pat. No. 5,475,525 to Tournois et al.

A patent to Bjork et al., U.S. Pat. No. 4,647,207 is disclosed as it describes an ellipsometer system which has provision for sequentially positioning a plurality of reflective polarization state modifiers in a beam of electromagnetic radiation. While said 207 Patent mentions investigating a sample system in a transmission mode, no mention or suggestion is found for utilizing a plurality of transmitting polarization state modifiers, emphasis added. Patent Nos. 4,210,401; 4,332,476 and 4,355,903 are also identified as being cited in the 207 Patent. It is noted that systems as disclosed in these patents, (particularly in the 476 Patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

Patents to Rosencwaig et al., U.S. Pat. Nos. 4,750,822 and 5,595,406 are also identified as they describe systems which impinge electromagnetic beams onto sample systems at oblique angles of incidence. The 406 Patent provides for use of multiple wavelengths and multiple angles of incidence. For similar reasons patent U.S. Pat. No. 5,042,951 to Gold et al. is also disclosed.

A patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other patents identified in a Search which identified said 918 Patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other patents are not believed to be particularly relevant, however.

A patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this patent is not controlling where electromagnetic radiation carrying fiber optics are present.

A patent to Chen et al., U.S. Pat. No. 5,581,350, is disclosed as it describes a method for regression calibration of ellipsometers which is very much similar to that disclosed earlier in an article by Johs.

Patent to Wang. et al., U.S. Pat. No. 6,587,282 is disclosed as it describes a three lens system with specific curvature and spacings associated with each of the lenses.

Patent to Uhrich et al., U.S. Pat. No. 6,829,049 is disclosed as it describes a broadband ellipsometer with all refractive optical system for focusing a probe beam onto a sample.

As present invention preferred practice is to utilize a spectroscopic source of electromagnetic radiation with a relatively flat spectrum over a large range of wavelengths U.S. Pat. No. 6,628,917 to Johs is disclosed. Patents relevant thereto include U.S. Pat. No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 Patent. Another patent, U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively. Another patent, U.S. Pat. No. 3,947,688 to Massey, describes a method of generating tuneable coherent ultraviolet light, comprising use of an electromagnetic electromagnetic beam combining system. A patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A patent to Wright, U.S. Pat. No. 5,002,371 is also mentioned as describing a beam splitter system which operates to separate "P" and "S" orthogonal components in a beam of polarized electromagnetic radiation.

Various papers were also identified as possibly pertinent, and are:

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Nijs & Silfhout, titled "systematic and Random Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (setp. 1994) describes first order corrections for imperfections in windows and compensators in Rotating Compensator ellipsometers.

Other papers of interest in the area by Azzam & Bashara include one titled "Unified Analysis of Ellipsometry Errors Due to Imperfect Components Cell-Window Birefringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment Of Optical Systems", J.O.S.A., Vol. 31, (July 1941), is also identified as it describes the characterizing of multiple lens elements which separately demonstrate birefringence, as a single lens, (which can demonstrate reduced birefringence).

A paper by Zapien et al., titled: "Real-Time Spectroscopic Ellipsometry from 1.5 to 6.5 eV", Thin Solid Films 364, (2000), shos lenses on both sides of a sample.

A paper by Li titled: "Flying Height Measurementon Al2O3 Film of a Magnetic Slider", J. or Tribiology, (October 1997) describes a 17 micron spot size achieved by a focusing lens.

A paper by Ghazzawi et al., titled: "Spectroellipsometry Characterization of Directly Bonded Silicon-On-Insulator Structures, Thin Solid Films 233 (1993).

Finally, a paper which is co-authored by inventors herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of relevant prior art, there remains need for ellipsometer systems which comprise input, and optionally output, lenses that allow focusing spectroscopic electromagnetic beams as small spots on material substrates. Further, in view of the inability of first order corrections to break birefringence based correlation between input and/or output lenses and a material system, there remains need for a second order mathematical model equation correction technique which enables breaking correlation between a material system characterizing DELTA and in-plane retardance entered to a beam of electromagnetic radiation by input and output lenses through which said beam of electromagnetic radiation is caused to pass. This is particularly true where lens birefringent retardance exceeds a few degrees. In addition, need remains for a lens system, and the method of its construction, which enables very precise lens characteristics realization The present invention provides a system with the identified attributes.

DISCLOSURE OF THE INVENTION

It is first emphasised that in U.S. Pat. No. 6,549,282, Ser. No. 09/419,794 Filed Oct. 18, 1999, in Col. 13, Lines 34–37, it was disclosed that in a two (input-output) lens system in an ellipsometer system, one lens which does not demonstrate birefringence can be a "phantom" lens which is essentially just the atmosphere surrounding a sample system. It is also disclosed directly following said language in said 282 Patent, that it is to be understood that input optical elements can comprise beam directing means . . . and that output optical elements can comprise beam directing means, (such as reflective optics). This is disclosed in view of a patent to Uhrich et al., U.S. Pat. No. 6,829,049 which was Filed May 3, 2001 with Priority Claimed from 60/204,253 which was filed in the year 2000. Said patent Claims all-refractive focusing optical system with lens elements mounted in a stress-minimizing-fixture. It is believe by the Inventors herein that the stress-minimizing mounting involving spacers between lenses in the context of an ellipsometer is the only patentable aspect of the 049 Patent. In fact, it is believed that said 049 Patent requires that all lenses be mounted in the shown manner. That is, for instance, were even one lens glued in place in said fixture, the stress minimizing property would be lost. In the context of the present Application then, a "stress" reducing" approach to mounting three or more lenses could provide that a spacer means be placed between two or more thereof as they are entered into a tube, and at least one lens be cemented in place. Continuing, the preferred embodiment of the present invention provides lenses, or multiple lens elements be mounted in a tube, but unlike the 049 mounting fixture, said tube has at least one hole through the wall thereof, and cement is applied through said at least one hole to secure at least one of said lenses or lens elements in place therewithin. While it is believed that the mounting technique of cementing at least one lense or lense element in place in the present invention does not induce undue stress in lenses, the focus of the present invention mounting system and method is the achievement of precise relative positioning between the Lenses or lense elements just before they are secured in the tube by applying cement. This is in contrast to mounting the lenses or lens elements in a manner to minimize stress induced therein by said mounting. That is, while causing unnecessary mounting stress in lenses is not believed to be a result of practicing the present invention, minimizing stress induced in lenses as a result of their mounting in said tube is not the primary goal of the present invention. As disclosed directly, the present invention places focus on providing lens mounting means which allow precise control of the relative positioning of multiple lenses with respect to one another before being cemented in place in a tube, (ie. fixture). While stress on lenses is not a desirable effect of a lens mounting fixture, the lens mounting "fixtures" of the present invention are not designed to produce undue stress or to minimize it, but rather are designed to allow precise relative positioning of lens elements therein, and securing said lens elements in place by entering cement through holes in the wall of the tube, once precise positioning of a plurality of lenses, (ie. multiple lens elements in a multiple-element-lens), is achieved.

The disclosed invention is an ellipsometer or polarimeter system comprising at least one multi-element lens placed at a selection from the group consisting of:

at the input; and at the output;

said at least one multi-element lens being comprised of at least two elements which are made of different materials, such that in use the focal length for each wavelength in a range of wavelengths is essentially the same for every other wavelength is said range of wavelengths, wherein said multi-element lens demonstrates at least some birefringence.

Preferred construction of said at least one multi-element lens provides three elements:
Calcium Fluouride;
Fused Silica;
Calcium Fluouride;
said elements being cemented to a mounting fixture instead of said Calcium Fluouride-Fused Silica-Calcium Fluouride elements being mounted to a lens mounting fixture which minimizes stress on the three lenses, in order to minimize stress induced birefringence.

Said ellipsometer or polarimeter further comprises a broadband source for generating a polychromatic probe beam and a polarizer prior to a sample; and an analyzer and detector after said sample, and in the case of a polarimeter, at least one compensator is present at, at least one location selected from the group consisting of:
before said sample; and
after said sample.

The disclosed invention can be described as a broadband ellipsometer or polarimeter system for evaluating the characteristics of a sample comprising:
a broadband light source for generating a polychromatic probe beam, said polychromatic probe beam comprising at least UV and Visible wavelengths; an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises at least one hole through the wall thereof for accepting cement;

such that at least first said lens is placed in said tube at the location of a hole for accepting cement and cement is entered thereinto and allowed to dry, thereby securing said lens in place in said tube; and such that an additional lens is mounted by a selection from the group consisting of:
being similarly cemented into place in said tube at a precise location with respect to said first lens; and
being positioned in said tube with respect to said first lens in a stress reducing manner comprising spacer means for maintaining relative position between said lenses;

said broadband ellipsometer or polarimeter system further comprising an analyzer system for monitoring at least a portion of a probe beam reflected from said sample, and generating output signals responsive thereto, and a processor for evaluating characteristics of the sample based on the output signals.

Said broadband ellipsometer or polarimeter system can comprise three lenses present in said tube, each thereof being located with respect to holes through the wall of said tube and secured in said position by cement which is entered into said holes. A preferred arrangement of lenses provides that bi-convex converging calcium flouride lenses disposed be opposite sides of a bi-concave diverging fused silica lens. In a practical sense said broadband ellipsometer includes at least one lens which demonstrates more than a minimized birefringence which would be possible were said at least one lens mounted in a lens mounting fixture for minimizing stress thereon to minimize stress induced birefringence in said at least one lens. That is, at least one of said at least two lenses is mounted in other than a stress minimizing manner, so as to minimize stress induced birefringence in said at least one lens, but rather is mounted in a "fixture" which allows precisely positioning lenses with respect to one another before securing them in place with cement. In fact, the preferred embodiment provides that the relative position between at least two of said at least two lenses in said tube be precisely controlled by, while actively monitoring of the effect of said at least two lenses on a beam of electromagnetic radiation caused to pass therethrough, adjusting said relative position until an acceptable effect is achieved, and wherein cement is only then entered through holes in the wall of said tube which are near edges of said at least two lenses, to secure the positions of said lenses.

The disclosed invention also includes a method of improving the operation of a broadband ellipsometer or polarimeter for evaluating the characteristics of a sample comprising:
a) providing broadband ellipsometer or polarimeter which comprises:
broadband light source means for generating a polychromatic probe beam, said polychromatic probe beam comprising at least UV and Visible wavelengths;
an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises holes through the wall thereof for accepting cement;
b) effecting the relative position between at least two of said at least two lenses in said tube by, while actively monitoring of the effect of said at least two lenses on a beam of electromagnetic radiation caused to pass therethrough, adjusting said relative position until an acceptable effect is achieved on said electromagnetic beam, and wherein cement is then entered through holes in the wall of said tube which are near edges of said at least two lenses, to secure the positions of said lenses;

such that said at least two lenses are precisely secured in said tube at desired locations relative to one another.

Said method can be practiced where there are three lenses present in said tube, each thereof being precisely located with respect to one another and secured in said position by cement which is entered into said holes through the wall of said tube when an acceptable effect on said beam of electromagnetic radiation is achieved. Said three lenses which are precisely positioned with respect to one another are preferably two convex calcium flouride lenses disposed on opposite sides of a fused silica lens. Further, there can four, or any number of lenses present.

A broadband ellipsometer or polarimeter for evaluating the characteristics of a sample can then be recited as comprising:
a broadband light source for generating a polychromatic probe beam, said polychromatic probe beam comprising at least UV and Visible wavelengths, an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises holes through the wall thereof for accepting cement;

such that lenses are placed in said tube at the location of said holes for accepting cement and cement is entered thereinto and allowed to dry, thereby securing said lenses in place;

said broadband ellipsometer or polarimeter system further comprising an analyzer system for monitoring at least a portion of a probe beam reflected from said sample and generating output signals responsive thereto, and a processor for evaluating characteristics of the sample based on said output signals;

said broadband ellipsometer or polarimeter being distinguished in that the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved on said beam of electromagnetic radiation, and wherein cement is then entered through at least one hole in the wall of said tube which is near an edge of at least one of said at least two lenses, to secure the positions of said lenses. All present lenses can be similarly secured in place in said tube, or at least one additional lens can be positioned with respect to a cemented in place lens via spacer means for effecting position between lenses in a stress reducing manner.

And again, said broadband ellipsometer or polarimeter can comprise, for instance, three lenses in which the relative position between the first and second, and between the second and third is precisely controlled prior to cementing them into position in said tube.

Where there are three lenses present having a combined focal length (F), the first lens can be a positive lens made from a first material, the second lens can be a negative lens made from a second material, and the third lens can be a positive lens made from a third material. Said three lenses can be considered to have "n" faces numbered 1–6, with "rn" being the radius of curvature of the nth face, and "tn" being the spacing nth and (n+1)st face. The preferred embodiment provides that at least one of said "r2" and/or "t4" be other than:

$|r2|<|F|$;

$|t4|>|0.05F|$.

And at least one of said "r4" and/or "r5" can optionally be other than:

$|r4|>|2.5F|$ $|r5|>|0.5F|$.

As previously presented in a Parent Application, the present invention system comprises a lens system, primarily as applied in ellipsometer and polarimeter systems wherein birefringence, and spectroscopic electromagnetic beam spot size chromatic dispersion reduction and focal length chromatic dispersion reduction is desired, but wherein spherical, coma distortion, third order aberations, astigmatism and image reproduction are of lesser importantance. A single stage present invention lens system can have a focal length of one-hundred millimeters or less, (nominally about eighty millimeters), and said lens system comprises two sequentially oriented elements, one of said two sequentially oriented elements being of a shape and orientation which individually converges a beam of electromagnetic radiation caused to pass therethrough, and the other being of a shape and orientation which individually diverges, (to a lesser degree than said convergence), a beam of electromagnetic radiation caused to pass therethrough, there being a region between said first and second elements. A present invention dual stage lens system provides a less than fifty millimeter, (nominal about forty millimeter), focal length and is comprised of four sequentially oriented lens elements which are grouped into two groups of two elements each, two of which four elements are converging and two of which are diverging of electromagnetic radiation caused to pass therethrough.

It is to be understood that, in use, a beam of electromagnetic radiation sequentially passes through one of said first and second elements in a single present invention lens system, then said region therebetween, and then through said second of said first and second elements before emerging as a focused beam of electromagnetic radiation, said region between said first and second elements have essentially the optical properties of a void region, or functional equivalent. In a dual stage present invention lens system a second stage of first and second elements is present in the electromagnetic beam pathway.

Further, present invention lens systems are characterized as quasi-achromatic as a result of multi-element construction, wherein, for each said two element lens systems present, the two elements thereof are made from different materials, (eg. one from what is commonly termed Crown-glass and one from Flint-glass in the literature). Again, as a result of present invention lens construction, very small electromagnetic beam spot focusing on an investigated material system is possible over a large range of wavelengths, (including transmitting properties into the deep UV), because of reduced chromatic focal length and spot size dispersion. It is noted that said present invention multi-element ellipsometer system input (and output) lenses can both (when present) demonstrate birefringence; neither demonstrate birefringence or one can demonstrate birefringence and the other not demonstrate birefringence. In fact, as disclosed in U.S. Pat. No. 6,549,282, Ser. No. 09/419,794 Filed Oct. 18, 1999, in Col. 13, Lines 34–37, one non-birefringent input or output lens can be absent but for a consideration of its presence as essentially surrounding atmospheric ambient, or equivalent thereto. That is, the concept of a multi-element focusing lens in an ellipsometer, without the presence of a recollimation lens therein, was disclosed in October 1999 by the present inventors, which is prior to the Filing Date of a patent to Uhrich et al., U.S. Pat. No. 6,829,049 which was Filed May 3, 2001 with Priority Claimed from 60/204,253 which was filed in the year 2000.

A present invention lens system, which is particularly well suited for application in ellipsometer systems, provides for spectroscopic electromagnetic beam spot size and focal length chromatic dispersion reduction by configuring at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation. Such a lens system with application in ellipsometer systems is characterized by a converging element which presents as a selection from the group consisting of:

a bi-convex;

a plano-convex with an essentially flat side;

and said diverging element is characterized as a selection from the group consisting of:

a bi-concave lens element;

a plano-concave with an essentially flat side.

Further said present invention lens systems can comprise a selection from the group consisting of:

a) at least one thereof comprises:
two sequentially oriented elements, one of said two sequentially oriented elements being of a shape and orientation which individually diverges a beam of electromagnetic radiation caused to pass therethrough, and the other being of a shape and orientation which individually converges a beam of electromagnetic radiation caused to pass therethrough,
there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation.

b) at least one thereof comprises:
a sequential combination of a bi-convex element and a bi-concave element.

c) at least one thereof comprises:
a sequential combination of a bi-concave element and a bi-convex element.

d) at least one thereof comprises:
a sequential combination of a bi-convex element and a plano-concave element with said concave side of said plano-concave element adjacent to said bi-convex element.

e) at least one thereof comprises:
a sequential combination of a bi-convex element and a plano-concave element with said essentially flat side of said plano-concave element being adjacent to said bi-convex element;

f) at least one thereof comprises:
a sequential combination of a plano-concave element and a bi-convex element with said essentially flat side of said plano-concave element adjacent to said bi-concave element;

g) at least one thereof comprises:
a sequential combination of a plano-concave element and bi-convex element with said concave side of said plano-concave element adjacent to said bi-convex element;

h) at least one thereof comprises:
a sequential combination of a plano-convex element and a bi-concave element with said essentially flat side of said plano-convex element adjacent to said bi-concave element;

i) at least one thereof comprises:
a sequential combination of a bi-concave element with a plano-convex element with said convex side of said plano-convex element adjacent to said bi-concave element;

j) at least one thereof comprises:
a sequential combination of a plano-concave element and a plano-convex element with the essentially flat side of said plano-concave element being adjacent to the convex side of the plano-convex element;

k) at least one thereof comprises:
a sequential combination of a plano-concave element and a plano-convex element with the essentially flat side of said plano-concave element being adjacent to the flat side of said plano-convex element;

l) at least one thereof comprises:
a sequential combination of a plano-convex element and a plano-concave element with the essentially flat side of said plano-covex element and the essentially flat side of said plano-concave element being adjacent to one another;

m) at least one thereof comprises:
a sequential combination of a plano-concave element and a plano-convex element with the concave side of said plano-concave element being adjacent to the convex side of the plano-convex element;

n) at least one thereof comprises:
a sequential combination of a plano-convex element bi-concave element with said convex side of said plano-convex element adjacent to said bi-concave element;

o) at least one thereof comprises:
a sequential combination of a bi-concave element and a plano-convex element with said essentially flat side of said plano-convex element adjacent to said bi-concave element;

p) at least one thereof comprises:
a sequential combination of a plano-convex element and a plano-concave element with said convex side of said plano-convex element adjacent to the concave side of the plano-concave element;

q) at least one thereof comprises:
a sequential combination of a plano-concave element and a plano-convex element with said essentially flat side of said plano-concave element being adjacent to the essentially convex side of the plano-convex element;

r) at least one thereof comprises:
a sequential combination of a plano-convex element and a plano-concave element with said convex side of said plano-convex element being adjacent to the essentially flat side of the plano-concave element;

s) at least one thereof comprises:
a sequential combination of a plano-concave element with a plano-convex element with the essentially flat side of said plano-convex element being adjacent to the concave side of said plano-concave element;

t) at least one thereof comprises:
at least one of the input and output lenses comprises at least two sequentially oriented elements, and is characterized by being a selection from the group consisting of:
a sequential combination of a converging element and a diverging element;
a sequential combination of a diverging element and a converging element;
a sequential combination of a converging element, a diverging element, a converging element and a diverging element;
a sequential combination of a converging element, a diverging element, a diverging element and a converging element;
a sequential combination of a diverging element, a converging element, a diverging element and a converging element;
a sequential combination of a diverging element, a converging element, a converging element and a diverging element;
includes a miniscus lens; and includes an aspherical lens;

u) at least one thereof comprises:
two elements with a region therebetween, wherein said region between said at least two elements has the optical properties of a selection from the group consisting of:
a void region; and
a functional equivalent to a void region;

v) at least one thereof comprises:
  at least two elements which are made from different materials independently selected from the group consisting of:
    $CaF_2$;
    $BaF_2$;
    LiF;
    $MgF_2$;
    fused silica;
    a void region;
    a gas filled region;
    a liquid filled region; and
    a functional equivalent to a void region.
and wherein each of said at least two elements are individually selected to be made of different materials;
w) at least one thereof is characterized by at least one selection from the group consisting of:
  a) the focal length is between forty and forty-one millimeters over a range of wavelengths of at least two-hundred to seven-hundred nanometers;
  b) the focal length varies by less than five (5%) percent over a range of wavelengths of between two-hundred and five-hundred nanometers; and
  c) the spot diameter at the focal length is less than seventy-five microns over a range of wavelengths of at least two-hundred to seven-hundred nanometers;
x) at least one thereof comprises:
  an element made of a selection from the group consisting of:
    $CaF_2$; and
    fused silica;
y) at least one thereof:
  is made of two elements, one of said elements being made of Fused Silica and the other of $CaF_2$;
z) at least one thereof comprises:
  a converging element selected from the group consisting of:
    a positive miniscus;
    an asymetric convex;

and/or a diverging element selected from the group consisting of:
  a negative miniscus;
  an asymetric concave.

A present invention lens system with application in ellipsometer systems can be further characterized in that the converging element of said first and second elements is typically made of a material independently selected from the group consisting of:
  $CaF_2$;
  $BaF_2$;
  LiF; and
  $MgF_2$;
  fused silica;
  a void region;
  a gas filled region;
  a liquid filled region; and
  a functional equivalent to a void region.

and the diverging element of said first and second elements is selected to be made of fused silica, although it is within the scope of the present invention to make the converging element of fused silica and the diverging element of a selection from the group consisting of $CaF_2$; $BaF_2$; LiF; and $MgF_2$. It is noted that lens elements made of $MgF_2$ are typically bi-refringent whereas lens elements made of $CaF_2$; $BaF_2$ and LiF typically demonstrate far less bi-refringence, unless subjected to stress.

A present invention lens system with a focal length of fifty millimeters or less, with application in ellipsometer systems, can be described as being comprised of lens system comprising two sequentially oriented lenses, each of said sequentially oriented lenses being comprised of:
  at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation; said lens system being described by a selection, as shown in FIGS. 1a25–1a28, from the group consisting of:
  1. a sequential combination of a converging element (C), a diverging element (D), a converging element (C) and a diverging element (D);
  2. a sequential combination of a converging element (C), a diverging (D) element, a diverging (D), element and a converging (C) element;
  3. a sequential combination of a diverging element (D), a converging element (C), a diverging (D) element and a converging (C) element;
  4. a sequential combination of a diverging element (D), a converging element (C), a converging element (C) and a diverging (D) element.

And, of course, other sequential lens element configurations within the scope of the present invention include:
  (Converging(C))(Diverging(D))(Converging(C));
  (Converging(C))(Converging(C)) (Diverging(D));
  (Diverging(D))(Diverging(D))(Converging(C));
  (Converging(C))(Diverging(D))(Diverging(D));
  (Diverging (D))(Converging(C))(Diverging(D));
  (converging(C))(Converging(C))(Diverging(D))(Diverging(D)); and
  (Diverging(D))(Diverging(D))(Converging(C))(Converging(C)).

One embodiment of a present invention lens system is further characterized by at least one selection from the group consisting of:
  a. the focal length of the lens system is between forty (40) and forty-one (41) millimeters over a range of wavelengths of at least two-hundred (200) to seven-hundred (700) nanometers; and
  b. the focal length of the dual stage lens system varies by less than five (5%) percent over a range of wavelengths of between two-hundred and five-hundred nanometers; and
  c. the spot diameter at the focal length of the lens system is less than seventy-five (75) microns over a range of wavelengths of at least two-hundred (200) to seven-hundred (700) nanometers.

(It is noted that the listing of single two element lens constructions (a) through (r) above provides insight to applicable converging and diverging lens element combinations in dual stage lens systems).

It is specifically noted that the present invention includes the case of an ellipsometer system in which only one of said multi-element input or output lenses is present, (typically only the input lens), and the case wherein both input and output lenses are present, but only one is of multiple element construction, and/or demonstrates bi-refringence.

A preferred present invention single two element lens system is constructed from a Bi-convex lens element made of $CaF_2$, (eg. JANOS Technology Inc. Part No. A1407-003), functionally combined with a Fused Silica Plano-Concave lens element, (eg. OptoSigma Inc. Part No. 012-0080), in a manner generally indicated by FIG. 1a3.

Continuing, it is further noted that various beam directing means, such as mirror systems, enable providing small, spectroscopically essentially undispersed, electromagnetic beam spot size at a material system, but that most such mirror systems are birefringent, in that they retard orthogonal components of a polarized electromagnetic beam reflecting therefrom, by different amounts.

Further, while present invention multi-element lenses in ellipsometric settings are typically relatively less birefringent and chromatically dispersive than are, for instance, electromagnetic beam directing mirror systems, in the case where a present invention multi-element input and/or output optical element(s) demonstrates birefringence, the present invention is further a method of accurately evaluating parameters in parameterized equations in a mathematical model of a system of spatially separated input and output elements, (herein beneficially, demonstratively, identified as lenses), as applied in an ellipsometry or polarimetry setting. Said parameterized equations enable, when parameters therein are properly evaluated, independent calculation of retardation entered by each of said multi-element input lens and said multi-element output lens to, or between, orthogonal components of a beam of electromagnetic radiation caused to pass through said input and output lenses. This provides utility in the form of enabling the breaking of correlation between retardation entered between orthogonal components in a spectroscopic electromagnetic beam by input and output lenses and by a material system under investigation. (It is to be understood that at least one of said multi-element input and output lenses in a present invention ellipsometer is often at least somewhat birefringent even though it is quasi-achromatic regarding focal length over a relatively wide wavelength range).

Continuing, said at least one multiple element lens present at least one location selected from the group consisting of:
between said polarizer and said stage for supporting a sample system; and
between said stage for supporting a sample system and said analyzer;

and positioned so that said beam of electromagnetic radiation transmits therethrough in use typically comprises at least two elements which are made from different materials, such that in use the focal length for each wavelength in a range of wavelengths is within an acceptable range of focal lengths. Said at least one multi-element lens is characterized by a selection from the group consisting of:

It is generally presented that achromatic lens systems are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently. Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

It is also noted that ideal lenses do not attenuate the magnitude of $r_p$ or $r_s$ orthogonal components, (or at least do not change their ratio, $r_p/r_s$), and also do not enter phase shift between $r_p$ or $r_s$ orthogonal components when said beam of electromagnetic radiation is caused to pass therethrough. While control of the effect of a lens on a ratio, $(r_p/r_s)$, of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc.

In summary, the present invention discloses that multi-element lenses can be produced that provide essentially constant focal lengths and small spot size over a large spectroscopic range of wavelengths, and that said multi-element lenses can be produced which demonstrate small birefringence.

With the just recited listing of lens construction in mind, it should be appreciated that the disclosed invention can comprise a spectroscopic ellipsometer sequentially comprising:
a) a source of a spectroscopic beam electromagnetic radiation;
b) a polarizer element;

in either order elements c and d:
c) optionally a compensator element;
d) said input lens;
e) a material system;

in either order elements f and g:
f) said output lens;
g) optionally a compensator element;
h) an analyzer element; and
i) a detector System.

As demonstrated in U.S. Pat. Nos. 5,929,995 and 5,969,818 beam directing means and/or windows can be located at least one selection from the group consisting of:
a) between said source of a spectroscopic beam electromagnetic radiation and said material system; and
b) between said material system and said detector system.

The disclosed invention san also be described as a system for monitoring change in:
the intensity of; and/or
the ratio of and/or
the phase between orthogonal components in;

a spectroscopic beam of electromagnetic radiation which is caused by interaction with a material system;

said system comprising at least one lens which is of multiple element construction and positioned so that beam of electromagnetic radiation transmits therethrough, wherein, at least two elements thereof are made from different materials, such that in use the focal length for each wavelength in a range of wavelengths is within an acceptable range of focal lengths;

said at least one multiple element lens being characterized by at least one selection from the group consisting of:
a) the focal length is between forty and forty-one millimeters over a range of wavelengths of at least two-hundred to seven-hundred nanometers;
b) the focal length varies by less than five (5%) percent over a range of wavelengths of between two-hundred and five-hundred nanometers; and
c) the spot diameter at the focal length is less than seventy-five microns over a range of wavelengths of at least two-hundred to seven-hundred nanometers;

Said at least one multiple element lens comprises at least two elements which are made from different materials independently selected from the group consisting of:
$CaF_2$;
$BaF_2$;
LiF;
$MgF_2$;
fused silica;
a void region;
a gas filled region;
a liquid filled region; and
a functional equivalent to a void region.

As the present invention approach is not to strive to avoid all stress-induced birefringence in lens(es) mounted in an ellipsometer or polarimeter system, but rather on mounting multiple lens elements precisely with respect to one another, need exists for compensating birefringence with develops in the lens system(s). In a basic sense, the present invention method of breaking correlation between retardation effects caused by present invention multi-element input and/or output lenses in an ellipsometer system, and retardation effects caused by an adjacent, otherwise ellipsometrically undistinguishable material system being investigated comprises, in any functional order, the steps of:

a. providing spatially separated input and output optical element (eg. lenses), at least one of said input output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system, the composition of said material system being sufficiently well known so that retardance entered thereby to a polarized beam of electromagnetic radiation of a given wavelength, which is caused to interact with said material system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said input and output lenses and said material system, comprising separate parameterized equations for independently calculating retardance entered between orthogonal components of a beam of electromagnetic radiation caused to pass through each of said input and output lenses and interact with said material system in a plane of incidence thereto; such that where parameters in said mathematical model are properly evaluated, retardance entered between orthogonal components of a beam of electromagnetic radiation which passes through each of said input and output lenses and interacts with said material system in a plane of incidence thereto can be independently calculated from said parameterized equations, given wavelength;

e. obtaining a spectroscopic set of ellipsometric data with said parameterizable material system present on the means for supporting a material system, utilizing a beam of electromagnetic radiation provided by said source of electromagnetic radiation, said beam of electromagnetic radiation being caused to pass through said input lens, interact with said parameterizable material system in a plane of incidence thereto, and exit through said output lens and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input lens, interact with said material system in a plane of incidence thereto, and exit through said output lens.

The end result of practice of said method is that application of said parameterized equations for each of said input lens, output lens and material system for which values of parameters therein have been determined in step f., enables independent calculation of retardance entered between orthogonal components of a beam of electromagnetic radiation by each of said input and output lenses, and said material system, at given wavelengths in said spectroscopic set of ellipsometric data. And, it is emphasized that said calculated retardance values for each of said input lens, output lens and material system are essentially uncorrelated.

It is further to be appreciated that one of said input or output lenses can be physically absent entirely, which is the equivalent to considering it to be simply surrounding ambient atmosphere with associated non-birefringent properties. As disclosed in Parent application Ser. No. 09/419,794, (now U.S. Pat. No. 6,549,282), Filed Oct. 18, 1999, (which has priority over patent to Uhrich et al., U.S. Pat. No. 6,829,049 which was Filed May 3, 2001 with Priority Claimed from 60/204,253 which was filed in the year 2000), in Col. 13, Lines 34–37, the language "providing spatially separated input and output lenses", covers the case where at least one of said input and output lenses demonstrating birefringence when a beam of electromagnetic radiation is caused to pass therethrough", is to be interpreted to include such a situation wherein a non-birefringent lens is simply atmospheric ambient or an optical equivalent. Additionally, it is to be understood that input optical elements can comprise beam directing means and window(s), (as in a vacuum chamber), in addition to input lens(es); and that output optical elements can comprise a selection from beam directing means and window(s), (as in a vacuum chamber), as well as, or in place of output lens(es). Beam directing means can include reflective optics on the output side of a sample.

As further discussed later herein, a modification to the just recited method can be to, (in the step d. provision of a mathematical model for said ellipsometer system and said input and output lenses and said parameterizable material system for each of said input and output lenses), provide separate parameterized mathematical model parameterized equations for retardance entered to each of said two orthogonal components of a beam of electromagnetic radiation caused to pass through said input and output lenses. When this is done, at least one of said orthogonal components for each of said input and output lenses is directed out of the plane of incidence of said electromagnetic beam onto said parameterizable material system. And, typically, though not necessarily, one orthogonal component will be aligned with the plane of incidence of said electromagnetic beam onto said parameterizable material system. When this is done, calculation of retardation entered between orthogonal components of said beam of electromagnetic radiation, given wavelength, by said input lens is provided by comparison of retardance entered to each of said orthogonal components for said input lens, and such that calculation of retardation entered between orthogonal components of said beam of electromagnetic radiation, given wavelength, by said output lens is provided by comparison of retardance entered to each of said orthogonal components for said output lens.

It is pointed out that the step f. simultaneous evaluation of parameters in said mathematical model parameterized equations for said parameterizable material system, and for said input and output lenses, is typically, though not necessarily, achieved by a square error reducing mathematical curve fitting procedure.

It is important to understand that in the method recited earlier, the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data typically involves obtaining data at a plurality of settings of at least one component selected from the group consisting of: (said analyzer and said polarizer). As well, it is to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

It is also to be understood that the step of providing separate parameterized mathematical model parameterized equations for enabling independent calculation of retardance entered by said input said output lenses between orthogonal components of a beam of electromagnetic radiation caused to pass through said input and output lenses preferably involves parameterized equations having a form selected from the group consisting of:

$ret(\lambda)=(K1/\lambda)$ $ret(\lambda)=(K1/\lambda)*(1+(K2/\lambda^2))$ $ret(\lambda)=(K1/\lambda)*(1+(K2/\lambda^2)+(K3/\lambda^4))$ A modified method of accurately evaluating parameters in parameterized equations in a mathematical model of a system of spatially separated input and output lenses, said parameterized equations enabling, when parameters therein are properly evaluated, independent calculation of retardation entered by each of said input lens and said output lens to at least one orthogonal component(s) of a beam of electromagnetic radiation caused to pass through said input and output lenses, at least one of said input and output lenses being birefringent, said method comprising, in a functional order, the steps of:

a. providing spatially separated input and output lenses, at least one of said input and output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system;

d. providing a mathematical model for said ellipsometer system and said input and output lenses and said material system, comprising, for each of said input lens and said output lens, separate parameterized equations for retardance for at least one orthogonal component in a beam of electromagnetic radiation provided by said source of electromagnetic radiation, which orthogonal component is directed out of a plane of incidence which said electromagnetic beam makes with said material system in use, and optionally providing separate parameterized equations for retardance for an in-plane orthogonal component of said beam of electromagnetic radiation, such that retardation entered to said out-of-plane orthogonal component, and optionally to said in-plane orthogonal component, of said beam of electromagnetic radiation by each of said input and output lenses, can, for each of said input and output lenses, be separately calculated by said parameterized equations, given wavelength, where parameters in said parameterized equations are properly evaluated;

e. obtaining a spectroscopic set of ellipsometric data with said material system present on the means for supporting a material system, utilizing a beam of electromagnetic radiation provided by said source of electromagnetic radiation, said beam of electromagnetic radiation being caused to pass through said input lens, interact with said material system in a plane of incidence thereto, and exit through said output lens and enter said detector system;

f. by utilizing said mathematical model provided in step d. and said spectroscopic set of ellipsometric data obtained in step e., simultaneously evaluating material system DELTA'S in correlation with in-plane orthogonal component retardance entered to said beam of electromagnetic radiation by each of said input and output lenses, and parameters in said mathematical model parameterized equations for out-of-plane retardance entered by said input lens and said output lens to a beam of electromagnetic radiation caused to pass through said input lens, interact with said material system in said plane of incidence thereto, and exit through said output lens.

Again, application of said parameterized equations for out-of-plane retardance entered by said input lens and said output lens to a beam of electromagnetic radiation caused to pass through said input lens, interact with said material system in said plane of incidence thereto, and exit through said output lens, for which values of parameters therein are determined in step f., enables independent calculation of retardance entered to said out-of-plane orthogonal component of a beam of electromagnetic radiation by each of said input and output lenses, given wavelength.

Also, again the step f. simultaneous evaluation of parameters in said mathematical model parameterized equations for calculation of retardance entered to said out-of-plane orthogonal component of a beam of electromagnetic radiation by each of said input and output lenses, given wavelength, and said correlated material system DELTA'S and retardance entered to said in-plane orthogonal component of a beam of electromagnetic radiation by each of said input and output lenses, is typically achieved by a square error reducing mathematical curve fitting procedure.

It remains, in the presently disclosed method, to provide values for parameters in the in-plane parameterized equations for retardance, in said mathematical model of a system of spatially separated input and output lenses. The presently disclosed method therefore further comprises the steps of:

g. providing a parameterized equation for retardation entered by said material system to the in-plane orthogonal component of a beam of electromagnetic radiation, and as necessary similar parameterized equations for retardation entered by each of said input and output lenses to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said material system and by said input lens and said output lens such that the correlation between material system DELTA'S and the retardance entered by said in-plane orthogonal component of a beam of electromagnetic radiation by each of said input and output lenses, at given wavelengths in said spectroscopic set of ellipsometric data, is broken.

The end result of practice of the immediately foregoing steps a.–h. is that application of said parameterized equations for each of said input lens, output lens and material system for which values of parameters therein have been determined in step h., enables independent calculation of retardance entered to both said out-of-plane and said in-plane orthogonal components of a beam of electromagnetic radiation by each of said input and output lenses, and retardance entered by said material system to said in-plane orthogonal component of said beam of electromagnetic radiation, at given wavelengths in said spectroscopic set of ellipsometric data.

As before for other parameter evaluation steps, the step h. simultaneous evaluation of parameters in said mathematical model parameterized equations for said in-plane retardation entered by said parameterized material system, and said input and output lenses, is typically achieved by a square error reducing mathematical curve fitting procedure.

If the material system present can not be easily parameterized, the presently disclosed method of accurately evaluating parameters in parameterized equations in a mathematical model of a system of spatially separated input and output lenses, provides that the following steps, g.–j. be practiced:

g. removing the material system from said means for supporting a material system positioned between said input and output lenses, and positioning in its place an alternative material system for which a parameterized equation for calculating in-plane retardance entered to a beam of electromagnetic radiation, given wavelength, can be provided;

h. providing a parameterized equation for retardation entered in-plane to an orthogonal component of a beam of electromagnetic radiation by said alternative material system which is then positioned on said means for supporting a material system positioned between said input and output lenses, and as necessary similar parameterized equations for retardation entered by each of said input and output lenses to the in-plane orthogonal component of a beam of electromagnetic radiation;

i. obtaining a spectroscopic set of ellipsometric data with said alternative material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system;

j. by utilizing said parameterized mathematical model for said input lens and said output lens provided in step d. and said parameterized equation for retardation entered by said alternative material system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative material system and by said input lens and said output lens, such that correlation between DELTA'S entered by said alternative material system and retardance entered by said in-plane orthogonal component of said beam of electromagnetic radiation, by each of said input and output lenses, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said input lens and said output lens;

The end result being that application of said parameterized equations for each of said input lens and output lens and alternative material system, for each of which values of parameters therein have been determined in step j., enables independent calculation of retardance entered to both said out-of-plane and said in-plane orthogonal components of a beam of electromagnetic radiation by each of said input lens and said output lens, and retardance entered by said alternative material system to said in-plane orthogonal component of a beam of electromagnetic radiation, at given wavelengths in said spectroscopic set of ellipsometric data.

As before, said presently disclosed method of accurately evaluating parameters in parameterized equations in a mathematical model of a system of spatially separated input and output lenses provides that in the step j. simultaneous evaluation of parameters in said mathematical model parameterized equations for said in-plane retardation entered by said parameterized material system, and at least said in-plane input lens and output lens, is typically achieved by a square error reducing mathematical curve fitting procedure.

As mentioned with respect to the first method of the present invention disclosed herein, the presently disclosed method of accurately evaluating parameters in parameterized equations in a mathematical model of a system of spatially separated input and output lenses provides that the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data involves obtaining data at a plurality of settings of at least one component selected from the group consisting of: (said analyzer and said polarizer). As well, it is again to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

Said presently disclosed method of accurately evaluating parameters in parameterized equations in a mathematical model of a system of spatially separated input and output lenses also provides that the step of providing separate parameterized mathematical model parameterized equations for enabling independent calculation of out-of-plane and in-plane retardance entered by said input said output lenses to said beam of electromagnetic radiation caused to pass through said input and output lenses involve parameterized equations having a form selected from the group consisting of:

$ret(\lambda) = (K1/\lambda)$ $ret(\lambda) = (K1/\lambda) * (1 + (K2/\lambda^2))$ $ret(\lambda) = (K1/\lambda) * (1 + (K2/\lambda^2) + (K3/\lambda^4))$ It is again noted that while the present invention can be practiced with any type "lenses", be there one or two of them, (ie. one, or both, of the input or output lenses can be essentially non-birefringent and even ambient), and while an input lens or output lens can be considered to be formed by a plurality of elements, (eg. two elements made of different materials such as Fused Silica and Calcium Fluoride), the step a. providing of spatially separated input and output lenses is best exemplified as being practiced by the providing of an ellipsometer system that has both input and output lenses present therein through which an beam of electromagnetic radiation is caused to convergently enter and exit in a recolliminated form, respectively.

Any method of the present invention can further involve, in a functional order the following steps a1.–a4:

a1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and a2. causing an unknown material system to be present on said means for supporting a material system;

a3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and a4. by utilizing said mathematical model for said input lens and said output lens in which parameter values in mathematical model parameterized equations, for each of said input lens and output lens have been fixed, simultaneously evaluating PSI'S and uncorrelated DELTA'S parameters for said unknown material system.

As in other steps in the present invention method in which parameter values are evaluated, it is again noted that the method of accurately evaluating parameters in parameterized equations in a mathematical model of a system of spatially separated input and output lenses in which said simultaneous evaluation of PSI'S and DELTA'S for said unknown material are typically achieved by a square error reducing mathematical curve fitting procedure.

As alluded to earlier, the step of providing spatially separated input and output lenses, at least one of said input and output lenses demonstrating birefringence when a beam of electromagnetic radiation is caused to pass therethrough, can involve one or both lens(es) which is/are not birefringent. And, said at least one lens which is not birefringent can be essentially a surrounding ambient, (ie. a phantom lens which is essentially just the atmosphere surrounding a material system).

It is noted that where parameters in parameterized equations for out-of-plane retardance equations have been determined, a focused version of the present invention method for accurately evaluating parameters in parameterized equations in a mathematical model of a system of spatially separated input and output lenses can comprise the steps of b1–b7:

b1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and b2. causing an unknown material system to be present on said means for supporting a material system;

b3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and b4. by utilizing said mathematical model for said input lens and said output lens in which parameter values in mathematical model parameterized equations, for each of said input lens and output lens have been fixed, simultaneously evaluating ALPHA'S and BETA'S for said unknown material system, (see the Detailed Description for definition of ALPHA'S and BETA'S);

b5. applying transfer functions to said simultaneously evaluated ALPHA'S and BETA'S for said unknown material system to the end that a data set of effective PSI's and DELTA's for a combination of said lenses and said material system is provided;

b6. providing a mathematical model for said combination of said lenses and said material system which separately accounts for the retardation effects of the presence of said lenses and said material system by parameterized equations; and b7. by utilizing said mathematical model for said combination of said lenses and said material system which separately accounts for the effects of the presence of at least said lenses by parameterized equations; and said data set of effective PSI's and DELTA's for a combination of said lenses and said material system, simultaneously evaluating actual PSI's and DELTA's for said unknown material system per se.

In the case, for instance, where the ellipsometer involved is a Rotating Analyzer, or Rotating Polarizer ellipsometer system, (but not where the ellipsometer involved is a Rotating Compensator System), it is noted that determination of "Handedness" is required. Therefore the foregoing method can include, as necessary, providing a mathematical model for said combination of said lenses and said material system which separately accounts for the retardation effects of the presence of said lenses and said material system by parameterized equations which further includes providing for the effects of Handedness. It is specifically stated that where the present invention approach of regressing onto effective PSI and DELTA values, (as determined in step b7.), is utilized, the mathematical model can be derived so that "Handedness" is accounted for in arriving at actual PSI's and DELTA's for said unknown material system per se.

As a general comment it is to be understood that separate PSI and DELTA values are achieved for each angle of incidence a beam of electromagnetic radiation makes with respect to a material substrate and for each wavelength utilized in a spectroscopic range of wavelengths.

Also, as the present invention methodology finds application in ellipsometer systems in which are present input and/or output lenses, the foregoing methods of use are recited utilizing specific reference to input and output lenses in ellipsometer systems. In general said methodology can be applied where any input and/or output optical elements are present.

Finally, while the forgoing has presented method steps in a logical to enhance disclosure, it is to be understood that the steps of any method recitation in this Specification can be practiced in any functional order and remain within the scope of the present invention.

The present invention will be better understood by reference to the Detailed Description Section of this Disclosure, with appropriate reference being has to the Drawings.

SUMMARY OF THE INVENTION

It is a primary purpose and/or purpose of the present invention to teach a multi-element lens system which comprises a plurality of lenses mounted in a Tube, at least one of which is held in place by cement or other firm securing means which is applied via the wall of said tube.

It is another objective and/or purpose of the present invention to describe a lens system which enables practice of focused beam small-spot spectroscopic ellipsometry over a large wavelength range, including in the Visible and into the deep UV, (eg. wavelengths down to and below 190 NM). Multi-element lenses which comprise elements made of different materials allow essentially the same focal length to be achieved over a wide wavelength range.

It is yet another objective and/or purpose of the present invention to provide a method of precisely positioning a plurality of lenses in a Tube prior to securing at least one thereof in place by applying cement or other firm securing means via the wall of said tube.

It is another primary objective and/or purpose yet of the present invention to provide methods, (as originally presented in Parent application Ser. No. 09/162,217 as regards compensating Vacuum Window Birefringence), for essentially eliminating birefringence achromatic effects of multiple element input and output lenses, (optionally in combination with other ellipsometrically indistinguishable elements), in the analysis of ellipsometric data obtained utilizing an ellipsometer system beam of electromagnetic radiation which passes through said lenses.

Other objectives and/or purposes will become apparent by reference to other sections of this Specification.

BRIEF DESCRIPTION OF THE DRAWINGS

FIG. 1a1 shows a general elemental configuration of an ellipsometer system which can be applied to investigate a material system (SS).

FIG. 1a2 shows a perspective view of another ellipsometer system configuration showing the presence of electromagnetic beam directing optical elements (PRI) and (PRO).

FIG. 1a3 shows construction of a quasi-achromatic multi-element lens which can be considered as present at AC1 or AC2 in FIG. 1a1.

FIG. 1a4 shows construction of a dual stage quasi-achromatic multi-element lens which can be considered as present at AC1 or AC2 in FIG. 1a1.

FIG. 1a5 shows a plot of spot diameter vs. wavelength which characterizes a dual stage quasi-achromatic multi-element lens as shown in FIG. 1a4, and of single stage fused silica and $CaF_2$ lenses.

FIG. 1a6 shows a plot of focal length vs. wavelength which characterizes a dual stage quasi-achromatic multi-element lens as shown in FIG. 1a4, and of single stage fused silica and $CaF_2$ lenses.

FIGS. 1a7–1a24 show various combinations of bi-concave, plano-concave, bi-convex and plano-convex lens elements which can comprise a present invention lens.

FIGS. 1a25–1a28 show various sequences of converging and diverging lens elements which can comprise a present invention dual lens system.

FIGS. 1b1–1b4 show, respectively, a positive miniscus lens; a negative miniscus lens; an aspheric convex lens and an aspheric concave lens.

FIG. 1c shows a top elevational view of the ellipsometer system of FIG. 1a2 in the region of the detector.

FIG. 2 shows a top view of the ellipsometer system of FIG. 1a2, showing the presence of optical elements (PRI) and (PRO).

FIG. 5 shows a conventional prior art ellipsometer system.

FIG. 6 shows a system, which can be used as (PRI) and/or (PRO), (shown in FIGS. 1a2 and 2), for changing the initial propagation direction of a beam of electromagnetic radiation without significantly changing the phase angle between orthogonal components thereof.

DETAILED DESCRIPTION

Turning now to the Drawings, there is shown in FIG. 1a1, a general elemental configuration of an ellipsometer system to which the present invention can be applied to investigate a material system (SS). Shown for reflection and transmission are:
- a. a Source of a beam electromagnetic radiation (LS);
- b. a Polarizer element (P);
- c. optionally a compensator element (C1);
- d. (additional element(s)) (AC1);
- e. a material system (SS);
- f. (additional element(s)) (AC2);
- g. optionally a compensator element (C2);
- h. an Analyzer element (A); and
- i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the present invention Disclosure, primarily input and output lenses, and that only one such lens might be present in an ellipsometer system, (typically the input lens (AC1)). FIG. 1a3 shows the preferred construction of a present invention single quasi-achromatic multi-element lens which can be considered as present at AC1 or AC2. Note the presence of two (2) lens elements (FE1) and (FE3), with FE2 being a third lense element, or a void or "air gap", or a material with functionally similar optical properties. FIG. 1a4 shows the construction of a present invention dual quasi-achromatic multi-element lens which can be considered as present at AC1 or AC2, with an element sequence of:

((Diverging(D))(Converging(C))(Converging(C))(Diverging(D));

as indicated in FIG. 1a28. In FIG. 1a4, it is to be understood that one, or both, of the two quasi-achromatic multi-element lens shown can be reversed left to right, (ie. replaced with a vertical mirror image), and remain within the scope of the present invention. Another embodiment provides that a sequence of lens elements be:

(Converging(C))(Diverging(D))(Converging(C))(Diverging(D));

as indicated in FIG. 1a25, which is achieved by providing a vertically oriented mirror image of the first lens system which is comprised of (FE1a) (FE2a) and (FE3a) in FIG. Ia4. Other arrangements are indicated in FIGS. 1a26 and 1a27.

Figure 7A:
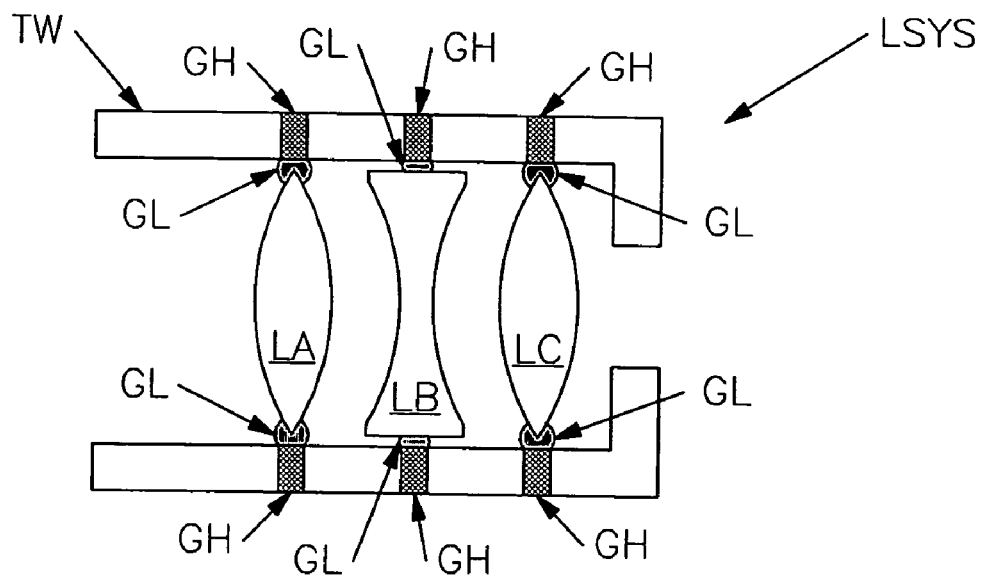
FIG. 7a shows a present invention three element lens, in which the three lenses are secured into a tube by cement applied through holes in the tube wall.
Figure 7B:
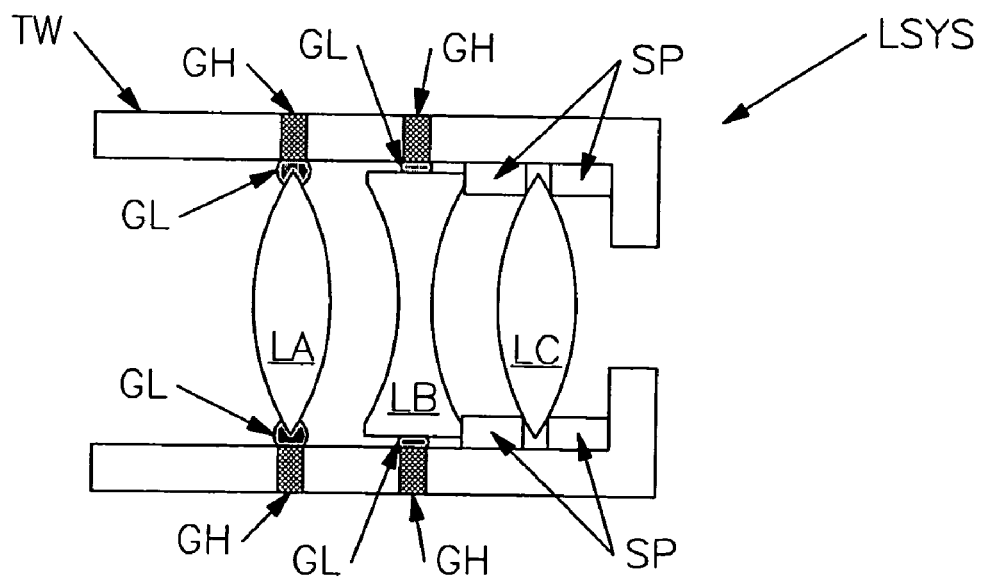
FIG. 7b shows a present invention three element lens system, in which the one lens is secured into a tube by cement applied through holes in the tube wall and two lenses are secured in said tube by stress reducing spacer means.

(Converging(C))(Diverging(D))(Diverging(D))(Converging(C)); and (Diverging(D))(Converging(C))(Diverging(D))(Converging(C));

And, of course, other configurations within the scope of the present invention include:

(Converging(C))(Diverging(D))(Converging(C)), (see FIGS. 7a and 7b);
(Converging(C))(Converging(C))(Diverging(D));
(Diverging(D))(Diverging(D))(Converging(C));
(Converging(C))(Diverging(D)) (Diverging(D));
(Diverging(D))(Converging(C))(Diverging(D));
(Converging(C))(Converging(C))(Diverging(D))(Diverging(D)); and
(Diverging(D))(Diverging(D))(Converging(C))(Converging(C)).

It should be appreciated that the additional elements in d. can then comprise selection(s) from the group consisting of:
beam directing means, (see (PRI) (PRO) in FIG. 1a2);
input lens(es); and
window(s), as in a vacuum chamber;

and the additional elements in f. can then comprise selection(s) from the group consisting of:
beam directing means, (see (PRI) (PRO) in FIG. 1a2);
output lens(es); and
window(s), as in a vacuum chamber.

As described with respect to FIG. 1a3, at least one of the input and output lenses, (generally represented by (AC1) and (AC2) in FIG. 1a1), can, when selected and present, be of multi-element (FE1) (FE3) construction, wherein, for each of said input and output lenses (AC1) and (AC2), when selected and present, at least two elements (FE1) and (FE3) thereof are made from different materials, such that in use the focal length for each wavelength in a range of wavelengths is essentially the same as that for every other wavelength, wherein at least one of said input and output lenses, when selected and present, demonstrates properties selected from the group consisting of:
both demonstrating birefringence;
neither demonstrating birefringence;
one demonstrating birefringence and the other not.

Representative materials from which different elements in said input and output lenses can be made are calcium fluoride (FE1) (FE1a) (FE1b), and fused silica (FE3), (FE3a) (FE3b).

Figure 3A:
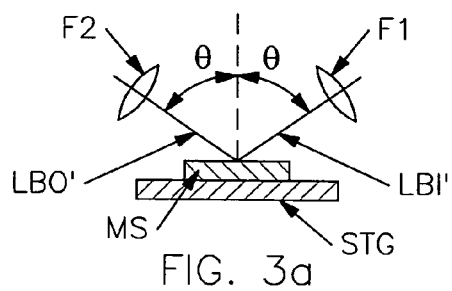
FIG. 3a shows a partial front elevational view of the ellipsometer system of FIG. 1a2.

Another embodiment of an ellipsometer system to which the present invention can be applied to further achieve smaller electromagnetic beam "Spot" size, is shown in FIGS. 1a2, 2 and 3a. FIG. 1a2 shows a Perspective view of a demonstrative system, FIG. 2 is a Top View, and FIG. 3a is a Front Elevational View. FIG. 1a2 shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Material System (MS) present on a Material System supporting Stage (STG). FIGS. 1a2 and 2 show that said interaction with the Surface (S) of said Material System (MS) causes a generally vertically oriented Polarized Beam of Electromagnetic Radiation (LBO') to pass through Focusing Optic (F2). FIGS. 1a2 and 2 show that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Material System (MS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

FIGS. 1b1–1b4 show, respectively, a positive miniscus lens; a negative miniscus lens; an aspheric convex lens and an aspheric concave lens. Said lens types can be utilized in the present invention at AC1 and/or AC2 and/or AC2' in FIG. 1a1; and at F1 and/or F2 in FIG. 1a2 in addition to or instead of lens configurations shown in FIGS. 1a3, 1a4 and 1a7–1a24.

FIG. 1c shows a more detailed, Top View, of a present invention Detector (DET) system as indicated in FIG. 1a2.

It is noted that (PRI) and (PRO) can be made of the same material, but the preferred embodiment provides that (PRI) be made of BK7 (refractive index approximately 1.55) and that (PRO) be made of F2 (refractive index approximately 1.7).

For demonstration purposes, FIG. 2 also shows, in dotted line form, Compensators (C) and (C'). When present one or more present Compensator(s) can be caused to rotate in use and the system is then a Rotating Compensator System and while obtaining data, both Polarizer (P) and Analyzer (A) are then held stationary. However, the Compensator(s) (C) and (C') can be absent or held stationary in use, and in use at least one of the Polarizer (P) and Analyzer (A) elements caused to rotate, thereby forming a Rotating Polarizer and/or Rotating Analyzer System. For the purposes of the present invention the specific element caused to rotate, or which is rotatable, in use is not a primary focus of patentability. Rather, it is the presence of lenses (F1) and (F2) which provide essentially constant focal lengths over a large range of wavelengths which constitutes the improvement.

FIG. 3a shows that as viewed in frontal elevation, generally vertically oriented Polarized Beams of Electromagnetic Radiation (LBI') and (LBO') approach and are reflected from, respectively, Material System (MS) at equal angles of Incidence and Reflection (θ) with respect to a normal to the upper surface of said Material System (MS). It is to be noted, as demonstrated by FIG. 3b, that a generally vertically oriented Polarized Beam of Electromagnetic Radiation (LBI') caused to be incident on a Material System (MS) at Seventy-Five (75) Degrees, (a typical Brewster Angle for Semiconductors), will "Spread" so that relative dimensions of the Beam "Spot" caused to appear on said Material System (MS) are One (1) by Four (4). Where the Angle of Incidence is set to Sixty-Five (65) Degrees, FIG. 3c shows that the Spot size is shown to have relative dimensions of One (1) by Two and one-half (2.5). This demonstrates that the closer to a Normal Angle of Incidence, (eg. (θ)=zero (0.0) Degrees), with respect to a Material System (MS) surface), a generally vertically oriented Polarized Beam of Electromagnetic Radiation (LBI') is caused to assume, the more "Concentrated" will be the Beam Intensity, and the smaller will be the Material System Investigating Spot Size. Higher Beam Intensity and Reduced Material System Investigating Spot Size are often both desirable features.

Figure 3B:
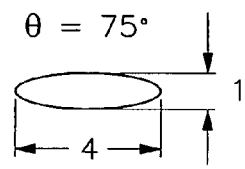
FIG. 3b shows a relative electromagnetic beam "Spot" size where an angle of incidence of seventy-five (75) degrees is utilized.
Figure 3C:
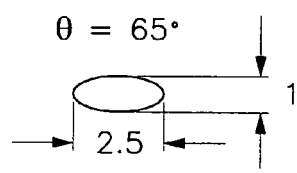
FIG. 3c shows a relative electromagnetic beam "Spot" size where an angle of incidence of sixty-five (65) degrees is utilized.

As regards the present invention, while FIGS. 3b and 3c demonstrate Beam "Spot" size reduction resulting from the control of the Angle-of-Incidence of an electromagnetic beam onto a material system, said FIGS. 3a and 3b can also be viewed and interpreted to demonstrate that at a constant angle of incidence, (whether provided by a FIG. 1a1 or FIG. 1a2 ellipsometer system configuration), different wavelengths in said Beam which pass through the Focusing Optics (AC1) (F1) can have different focal points, and the resulting "Spectral Spread" can lead to a FIG. 3b increased "Spot" size, thereby making it impossible to simultaneously, spectroscopically, investigate a small area on the substrate. An ideal situation therefore is achieved where the Focusing Optics (AC1) (F1) is achromatic, as provided by multi-element lenses such as shown in FIG. 1a3, where element (FE1) is made of a different material than is element (FE3) and where (FE2) is an air gap or equivalent. Such lenses can provide focal lengths which do not significantly change with wavelength, hence provide reduced "Spot" size. Lenses without radial symmetry can also effect change as between FIGS. 3b abd 3c.

Figure 4A:
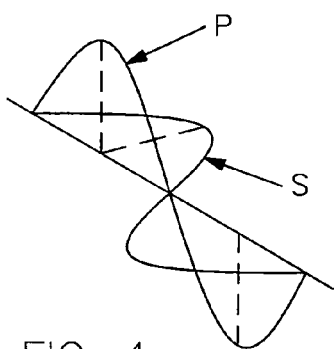
FIG. 4a shows "in-phase" components of a polarized beam of electromagnetic radiation.
Figure 4B:
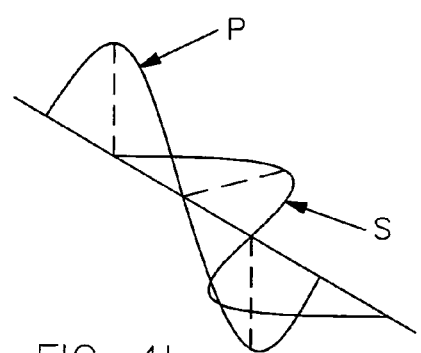
FIG. 4b shows "ninety-degree-out-of-phase" components of a polarized beam of electromagnetic radiation.
Figure 5:
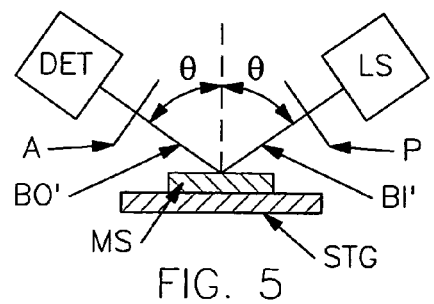
Figure 6:
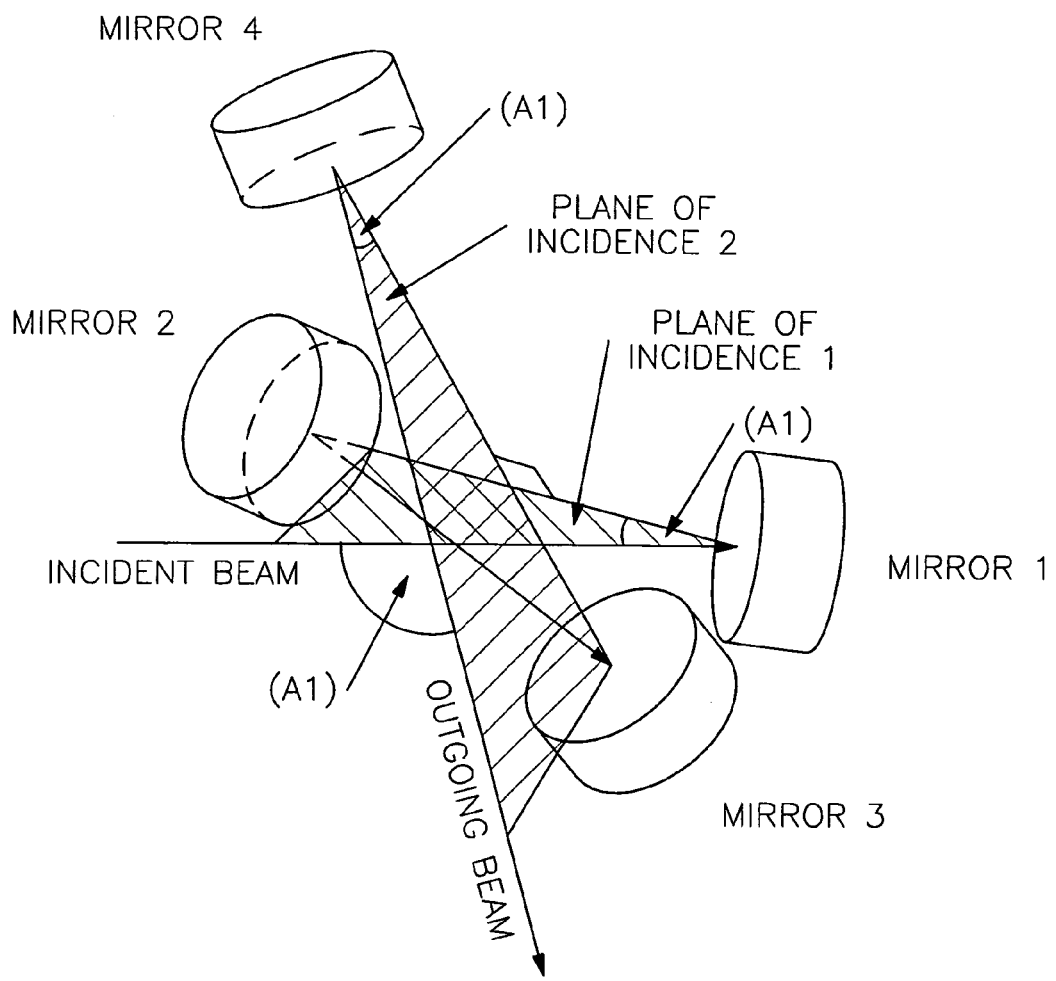

It is further noted that FIGS. 1a5 and 1a6 show plots of Spot Size and of Focal Length respectively, verses Wavelength for a Dual Quasi-Achromatic Multi-Element Lens as demonstrated in FIG. 1a4, (which can be considered as present at AC1 or AC2 in FIG. 1a1 and at F1 and/or F2 in FIG. 1a2). Shown also are curves of "Spot Size" and of "Focal Length" verses Wavelength for Fused Silica alone and for Calcium Fluoride ($CaF_2$) alone, and for a lens as shown in FIG. 1a4 where element (FE3) is Fused Silica and element (FE1) is Calcium Fluoride ($CaF_2$). Note the relatively more constant result for a multi-element lens as shown in FIG. 1a4 as compared to the results for single element lenses made from Fused Silica (FE3) and for Calcium Fluoride (FE1).

It is generally presented that achromatic lens systems, as demonstrated in FIGS. 1a3 and 1a4, are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently. Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

Continuing, for general insight, a shortcoming of Rotating Element Ellipsometer Systems, (other than Rotating Compensator Ellipsometers), generally is that certain Magnitudes of well known Material System characterizing PSI or DELTA can not be monitored thereby. For instance, in Rotating Analyzer Ellipsometer Systems, Material Systems with DELTA near zero (0.0) or one-hundred-eighty (180) Degrees can not be measured. It is also noted that Thin Dielectric Films, such as Nitride and oxide on semiconductor substrates, often present with a DELTA of one-hundred-eighty (180) Degrees at Angle of Incidence of less than the Brewster Angle, (eg. sixty-five (65) Degrees). The ellipsometer system shown in FIG. 1a2 recognizes. this problem and can utilize first and/or second Optical Elements, (eg. Prisms), (PRI) and (PRO) which effect Phase Angle Retardation between "P" and "S" Orthogonal Components of a Polarized Beam of Electromagnetic Radiation caused to pass therethrough. (Note that a "P" Component of a Polarized Beam of Electromagnetic Radiation is that Component found to be in a Plane containing both an Incident Beam of Electromagnetic Radiation and a Normal to a Material System Surface, while an "S" Component is that Component perpendicular to said "P" Plane and Parallel to the Material System Surface). The Phase Angle Retardation between "P" and "S" Orthogonal Components of a Polarized Beam of Electromagnetic Radiation caused to pass therethrough can be caused to Nominally Forty-Five (45) Degrees for each Optical Element (PRI) and (PRO) shown in FIG. 2, for a total of a Nominal Ninety (90) Degrees. This added Retardation between "P" and "S" Orthogonal Components serves to shift the Material System DELTA's which a Rotating Analyzer Ellipsometer will be unable to measure to Ninety (90) and Two-Hundred-Seventy (270) Degrees. Again, most Thin Film Material Systems present a DELTA of near zero (0.0) and one-hundred-eighty (180) Degrees, hence the first and second Optical Elements (PRI) and (PRO) serve not only to direct a Polarized Beam of Electromagnetic Radiation as desired, but also serve to "Condition" said Polarized Beam of Electromagnetic Radiation so that it can be utilized to measure Material System DELTA's which are in the range of near zero (0.0) Degrees or near one-hundred-eighty (180) degrees.

While FIG. 2 shows each of the first and second Optical Elements (PRI) and (PRO) as providing a total internal reflection angle of ninety (90) degrees, so as to direct said generally vertically oriented Incident Polarized Beam of Electromagnetic Radiation (LBI') at Ninety (90) Degrees with respect to said generally horizontally oriented Polarized Beam of Electromagnetic Radiation (LBI), and so as to direct said generally horizontally oriented Polarized Beam of Electromagnetic Radiation (LBO) at Ninety (90) Degrees with respect to said generally vertically oriented Polarized Beam of Electromagnetic Radiation (LBO'), other Optical Elements which provide other Angles between Incident and internally Reflected Beams of Electromagnetic Radiation can also be adapted for use in the present invention, and said usage is within the scope of the present invention. In such a case the terminology "generally horizontally oriented" and "other than generally horizontally oriented" serves to describe the relationship between incident and reflected beams of electromagnetic radiation. As well, Optical Elements which introduce other than essentially forty-five (45) degrees of retardation between "P" and "S" components of a Polarized Beam of Electromagnetic Radiation at a point of total internal reflection can be utilized. For instance, in a Rotating Compensator Ellipsometer System, as close to zero (0.0) degrees of entered retardation at a reflection as is possible might be desirable.

It should also be recognized that the presence of first and second Optical Elements (PRI) and (PRO) allow realization of a more laterally compact Ellipsometer or Polarimeter System Design, in that, as shown in FIG. 2, the Source of Electromagnetic Radiation (LS) and Detector (DET) can be placed as shown, rather than to the Right and Left of the Material System (MS) as is typical in most Ellipsometer Systems.

FIGS. 4a and 4b show "P" and "S" Components of a Polarized Beam of Electromagnetic Radiation for both "In-Phase" and "Ninety (90) Degrees Retardation" therebetween, respectively.

FIG. 5 is included to provide a reference to conventional ellipsometer and polarimeter and the like Material System investigation systems reported in the prior art. Note that a Light Source (LS), Polarizer (P), Material System (MS) Analyzer (A) and Detector (DET) are shown, as well as Incident (BI') and Reflected (BO') Electromagnetic Radiation Beams, (which are respectively, analogically, similarly positioned as are (LBI') and (LBO') in FIG. 3a). The region of FIG. 5 in the vicinity of the Material System (MS) is very much like what is shown in FIG. 3a, but for the fact that a smaller Beam "Spot" size will be effected by a FIG. 3a system by lens (F1). Note also that the placement of the Light Source (LS) and Detector (DET) in FIG. 5 are shown to be necessarily very different from that shown in FIGS. 1a3 and 2, as the present invention first and second Optical Elements (PRI) and (PRO), shown in FIGS. 1a2 and 2, are not present. It is noted that adjustment of Light Source (LS) and Detector (DET) positioning to allow different Angles-of-Incidence (θ) to be achieved is inherently more difficult in a system fashioned after FIG. 5, (or after FIG. 1a1), than it is in a present invention system fashioned after FIGS. 1a2 and 2.

For purposes of applying the present invention methodology, in that as (PRI), (F1), (F2) and (PRO) remain stationary during use in data acquisition, it should be appreciated that the FIG. 1a2 (PRI) and Convergent Input Lens (F1) can be considered a composite system, as can (PRO) and divergent output lens (F2). The Claims should be interpreted to include ellipsometrically indistinguishable elements within the terminology "input lens" or "output lens", where applicable. (Note that the paper by Jones referenced in the Background Section of this Specification describes why birefringence from ellipsometrically indistinguishable elements can be mathematically lumped together).

Also, as shown in application Ser. No. 09/144,764, filed Aug. 31, 1998, specific beam folding optics in which specific (PRI) and (PRO) embodiments are described. Each of the (PRI) and (PRO) can comprise first and second systems which each comprise two pairs of reflecting means, between which first and second systems is positioned a material system. FIG. 6 shows a system, which can be used as (PRI) and/or (PRO), for changing the initial propagation direction of a beam of electromagnetic radiation without significantly changing the phase angle between orthogonal components thereof, comprises two pairs of reflecting means, (MIRROR 1) and (MIRROR 2), oriented so that said initial beam of electromagnetic radiation (INCIDENT BEAM) reflects from a first reflecting means (MIRROR 1) in the first pair of reflecting means to a second reflecting means (MIRROR 2) in said first pair of reflecting means, in a first plane, (PLANE OF INCIDENCE 1), and such that the beam of electromagnetic radiation which reflects from said second reflecting means in said first pair of reflecting means is directed to a first reflecting means (MIRROR 3) in the second pair of said reflecting means, and reflects from said first reflecting means (MIRROR 3) in said second pair of reflecting means to a second reflecting means (MIRROR 4) in said second pair of reflecting means, in a second plane (PLANE OF INCIDENCE 2), which is essentially orthogonal to said first plane; such that the direction of propagation of the beam of electromagnetic radiation reflected from the second of the reflecting means in the second pair of reflecting means is different from the propagation direction of the initial beam of electromagnetic radiation; the basis of operation being that changes entered to the phase angle between orthogonal components of a beam of electromagnetic radiation by the first of said pairs of reflecting means are effectively canceled by said second pair of reflecting means.

Allowed application Ser. No. 09/162,217 filed Sep. 29, 1998, and Allowed application Ser. No. 09/033,694 filed Mar. 3, 1998 provide additional insight, and Allowed application Ser. No. 09/144,764, filed Aug. 31, 1998 are incorporated hereinto by reference. In particular the 217 Application shows application of the present invention methodology, wherein vacuum chamber windows, at least one of which demonstrates birefringence, (instead of input and output lenses), are investigated. The 694 Application provides experimental support for operational aspects of the FIG. 1a3 ellipsometer system configuration, and the 764 Application shows specific beam folding systems.

FIG. 7a demonstrates a present invention Lens System (LSYS) with Three Element (A) (B) and (C), (eg. Three (3) Lenses System), in which the three lenses are secured into a Tube (T) by Cement (GL) applied through Holes (H) in the Tube Wall (TW). It is noted the FIG. 7a approach to mounting multiple lenses is not focused on minimizing birefringence caused by stress, but rather on enabling precise relative positioning of lenses, and fixing them in place. No mounting system can provide an absolutely stress free mounting of multiple lenses, and it is accurate to state that all practical lenses demonstrate some level of birefringence, and any mounting means can enter stress to a lens. In that sense, the mounting system is not stress-minimizing. FIG. 7b shows a present invention Three (3) Element Lens System (LSYS), in which the lenses (LA) and (LB) are secured into a Tube by Cement (GL) applied through Holes (GH) in the Tube Wall (TW), and Lens (LC) is secured in position in said Tube by Stress Reducing Means comprising Spacers (SP). It is again emphasized that the approach to mounting the Lenses (LA) (LB) and (LC) demonstrated is not Stress Minimizing, but can be described as Stress Reducing. Of course a modification of this system might provide that Lenses (LA) and (LC) be cemented in place, with only Lens (LB) secured in place by Spacers (SP). And additional Lenses, (ie. Lense Elements), can also be present. The distinguishing factor is that at least one Lens present in the Tube is secured in place via Cement (GL) entered via Holes (GH) through the Tube Wall.

It is to be understood that, for the purposes of this Specification (AC2) and (AC2') in FIG. $1a_1$, and (F2) in FIGS. $1a_2$ and FIG. 2 and FIG. 3a, can be considered to be "Phantom Lenses" as originally disclosed in Parent application Ser. No. 09/419,794 Filed Oct. 18, 1999, (now U.S. Pat. No. 6,549,282). In Col. 13, Lines 34–37 of said 282 Patent, it is stated that in a two (input-output) lens system in an ellipsometer system, one lens which does not demonstrate birefringence can be a "phantom" lens which is essentially just the atmosphere surrounding a sample system. That is, in effect, only Lens (AC1) in FIG. $1a_1$, and (F1) in FIGS. $1a_2$ and FIG. 2 and FIG. 3a is present.

In summary, the present invention discloses that multi-element lenses can be produced that provide essentially constant focal lengths and small spot size over a large spectroscopic range of wavelengths, and that said multi-element lenses can be produced which demonstrate small birefringence. The present invention also teaches, however, that any birefringent effects presented by a present invention multi-element lenses, (and any ellipsometically non-distinguishable adjacent elements such as vacuum system windows and/or beam directing means), can be de-correlated from material system PSI and DELTA results, by practice of a methodology originally developed for acquiring ellipsometric data through vacuum chamber windows and initially disclosed in Parent application Ser. No. 09/162,217. The key insight enabling said accomplishment is that lens bi-refringence can be split into "out-of-plane" and "in-plane" components, where the "plane" referred to is the plane of incidence of an electromagnetic beam of radiation with respect to a material system. Splitting the lens birefringence into said orthogonal components allowed derivation of second order lens corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a material system DELTA. A separate step, utilizing a material system for which retardation can be modeled by a parameterized equation, allows evaluation of the parameters in parametric equations for the "in-plane" components of lenses separately. Work reported in the literature by other researchers regarding analogically similar window corrections provided equations which corrected only first order effects, and said equations have proven insufficient to correct for large, (eg. six (6) degrees), of retardation. (It is noted that prior work with respect to vacuum window corrections, orthogonal components were derived with respect to window fast axes, which is offset from the material system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a material system DELTA parameter unless a global regression fit using a parameterizable material system is performed at calibration time.

The present invention methodology comprising two steps disclosed herein, fully and unambiguously determines lens correction terms.

After parameters in parameterized equations for retardance are evaluated by the method of the present invention, ellipsometric data can be taken through lenses, (eg. input and output), and said data can be quickly and accurately analyzed by applying the correction factors in a mathematical model for a material system, (in the case where a Rotating Analyzer ellipsometer system was used to acquire data), or the lens effects can be simply quantitatively subtracted away to yield "true" ellipsometric PSI and DELTA values, (in the case where a Rotating Compensator ellipsometer system was used to acquire data).

It is to be appreciated that the correlation breaking methodology of the present invention is substantially the same as that disclosed in the Parent application Ser. No. 09/162,217 filed Sep. 29, 1998, with the difference being that the present invention provides compensation to input, and output, lenses, (perhaps in combination with beam directing optics), rather than, or in addition to, to vacuum chamber windows, (which can be present as mathematically lumped-in with FIG. 1a1 (AC1) and (AC2) input and output lenses, as described by the Jones reference disclosed in the Background Section). It is also noted that while achromatic multi-element input and output lenses are preferred for application in the present invention, any lenses can be applied where correlation breaking techniques are applied.

It is generally noted that the terminology "positive" or "+", as used to identify a lens means it is converging, whereas the terminology "negative" or "−", as used to identify a lens means it is diverging.

It is emphasized that a system of spatially separated input and output lenses can provide that at least one lens which is not significantly birefringent is selected from the group consisting of: (essentially a surrounding ambient; and a multi-element lens). That is, it is within the scope of the present invention to interpret simple ambient atmosphere as being an input or output lens, and where Claims recite the providing of separated input and output lenses, it should be kept in mind that one of said input and output "lenses" can be effectively the effective absence of any per se. lens. In that light it is emphasized that a present invention ellipsometer system can include a focusing input lens but not an output lens and be an acceptable present invention configuration. That is, while the foregoing disclosure often alludes to the presence of both input and output lenses, said language is to be interpreted generally to include cases wherein only one of said lenses is present, and the other lens is but ambient atmosphere.

It is to be understood that the foregoing presented numerous specific examples of lenses and systems which are non-limiting. For instance, where Claims do not recite specific lens construction, any functional lens construction is to be considered within the scope thereof. That is, while FIGS. 1$a$3, 1$a$4 and 1$a$7–1$a$28 show lens constructions which are preferred, said specific examples are not to be interpreted as limiting in, for instance, Method Claims for accurately evaluating parameters in parameterized equations in a mathematical model of a system of spatially separated input and output optical elements. Claims which do not recite specific lens construction are not to be read as limited by specific examples shown, where functional equivalents can be successfully applied. For instance, it is specifically noted that either void region, FE2$a$ or FE2$b$, in FIG. 1$a$4 can be absent, as where elements FE1$a$ and FE3$a$ make direct contact over their mid-region, and/or where FE1$b$ and FE3$b$ make direct contact over their mid-region thereof. This can occur, for instance, where the convex curvature of lens element FE1$a$ is the same as the concave curvature of element FE3$a$ in FIG. 1$a$3. Additionally, while preferred lenses applied in the present invention, as shown in FIG. 1$a$3, comprise two elements, where specific lens construction is not recited in a Claim, it is to be understood that any number of, and type of, elements can comprise a lens, (eg. comprise more than two elements, comprise meniscus and/or aspheric elements with radial or non-radial symetry).

It is further specifically noted that while the lenses shown in FIGS. 1$a_3$, 1$a_4$ and 1$a_7$–1$a_{28}$ are typically selected to demonstrate radial symetry, it is within the scope of the present invention to utilize non-radially symetric lenses, where, for instance, a spot size length to width aspect ratio is to be modified thereby. Therefore any lens shown or indicated in FIGS. 1$a_3$, 1$a_4$ and 1$a_7$–1$a_{28}$ can be designed to demonstrate radial symetry, or non-radial symetry, or be of any other functional type, where the achromatic properties are present. And, it is to be understood that FIGS. 1$a_3$, 1$a_4$, 1$a_7$–1$a_{28}$ and 7$a$ and 7$b$ are to be interpreted in the sense of the terminology "comprising". That is, while, for instance, FIG. 1$a_7$ show two elements, it can be interpreted to be a two element lens per se., or to be part of a three or more element lens. As an example, FIG. 1$a_7$ shows two lenses of the three lens system of FIGS. 7$a$ and 7$b$.

It is also to be understood that terminology such as "multi-element lenses" and the terminology "multiple lenses" system are used interchangeably in this Specification. That is, a lens system can be considered to be comprised of multiple elements or of multiple lenses and refer to the same system.

It is further to be understood that while cement entered through holes in a tube wall has been used as an exemplary preferred primary present invention means of securing a lens, or lens element(s) in place after appropriate positioning, it is within the scope of the present invention to firmly secure a lens or lens element(s) to the inner wall of a tube by securing means other than cement, with said "other securing means" being interpreted sufficiently broadly to include crimping or set-screws and other functional equivalents.

It is also specifically stated that it is believed that where at least one of at least two lenses in a multi-lens, (or elements in a multi-element lens system), is mounted in other than a manner specifically designed for—minimizing stress—thereon in order to minimize stress induced birefringence in said system, particularly where the lenses or lens elements are glued into a tubular fixture, then said lense system, in the context of application in an ellipsometer or polarimeter, is patentable.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer or polarimeter system comprising at least one multi-element lens placed at a selection from the group consisting of:
   at the input; and
   at the output;
said at least one multi-element lens being comprised of at least two elements which are made of different materials, such that in use the focal length for each wavelength in a range of wavelengths is essentially the same for every other wavelength is said range of wavelengths, wherein said multi-element lens demonstrates at least some birefringence; said at least one multi-element lens being sequentially comprised of at least first and second elements which are each independently selected from the group consisting of:
   $Ca_2$;
   $BaF_2$;
   LiF;
   $MgF_2$;
   fused silica;
   a void region;
   a gas filled region;
   a liquid filled region; and
   a functional equivalent to a void region;
said elements being cemented into a mounting fixture which comprises a tube with holes through the wall thereof through which cement is entered to secure said at least first and second elements, such that at least one of said lens elements is mounted in other than a manner specifically designed for minimizing stress thereon to minimize stress induced birefringence in said multi-element lens.

2. An ellipsometer or polarimeter system comprising at least one multi-element lens as in claim 1, in which the sequence of lenses is characterized by a selection for the group:
   (Converging(C))(Diverging(D))(Converging(C));
   (Converging(C))(Converging(C))(Diverging(D));

(Diverging(D))(Diverging(D))(Converging(C));
(Converging(C))(Diverging(D))(Diverging(D));
(Diverging(D))(Converging(C))(Diverging(D));
(Converging(C))(Converging(C))(Diverging(D))(Diverging(D));
(Diverging(D))(Diverging(D))(Converging(C))(Converging(C));
((Diverging(D))(Converging(C))(Converging(C))(Diverging(D));
(Converging(C))(Diverging(D))(Converging(C)) (Diverging(D));
(Converging(C))(Diverging(D))(Diverging(D))(Converging(C)); and
(Diverging(D))(Converging(C))(Diverging(D))(Converging(C)).

3. An ellipsometer or polarimeter as in claim 1, in which the at least one multi-element lens is sequentially comprised of three elements:
Calcium Fluouride;
Fused Silica;
Calcium Fluouride;
said Calcium Fluouride-Fused Silica-Calcium Fluouride elements being cemented into a mounting fixture which comprises a tube with holes through the wall thereof through which cement is entered to secure said three elements, such that at least one of said lens elements is mounted in other than a manner specifically designed for minimizing stress thereon to minimize stress induced birefringence in said multi-element lens.

4. An ellipsometer or polarimeter as in claim 1, which further comprises a broadband source for generating a polychromatic probe beam and a polarizer prior to a sample; and an analyzer and detector after said sample.

5. An ellipsometer or polarimeter as in claim 1, which further comprises a broadband source for generating a polychromatic probe beam and a polarizer prior to a sample; and an analyzer and detector after said sample, said polarimeter further having at least one compensator present at, at least one location selected from the group consisting of:
before said sample; and
after said sample.

6. An ellipsometer or polarimeter system comprising at least one multi-element lens placed at a selection from the group consisting of:
at the input; and
at the output;
said at least one multi-element lens being comprised of at least two elements which are made of different materials, such that in use the focal length for each wavelength in a range of wavelengths is essentially the same for every other wavelength is said range of wavelengths, at least one of said elements being cemented into a tube which comprises at least one hole through the wall thereof for entering said cement;
said ellipsometer or polarimeter system further comprising a broadband source for generating a polychromatic probe beam and a polarizer prior to a sample, and an analyzer and detector after said sample; and said polarimeter further having at least one compensator present at, at least one location selected from the group consisting of:
before said sample; and
after said sample.

7. A broadband ellipsometer or polarimeter for evaluating the characteristics of a sample comprising:
a broadband light source for generating a polychromatic probe beam, said polychromatic probe beam comprising at least UV and Visible wavelengths; an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises at least one hole through the wall thereof for accepting cement; such that at least a first said lens is placed in said tube at the location of a hole for accepting cement and cement is entered thereinto and allowed to dry, thereby securing said lens in place in said tube; and such that an additional lens is mounted in said tube by a selection from the group consisting of:
being similarly cemented into place in said tube at a precise location with respect to said first lens; and
being positioned in said tube with respect to said first lens in a stress reducing manner comprising spacer means for maintaining relative position between said lenses;
said broadband ellipsometer or polarimeter system further comprising an analyzer system for monitoring at least a portion of a probe beam reflected from said sample and generating output signals responsive thereto, and a processor for evaluating characteristics of the sample based on said output signals.

8. A broadband ellipsometer as in claim 7 in which there are three lenses present in said tube, each thereof being located with respect to holes through the wall of said tube and secured in said position by cement which is entered into said holes.

9. A broadband ellipsometer as in claim 8 in which the three lenses are two calcium flouride lenses disposed on opposite sides of a fused silica lens.

10. A broadband ellipsometer or polarimeter as in claim 8, in which there are three lenses having a combined focal length (F), the first lens being a positive lens made from a first material, the second lens being a negative lens made from a second material, and the third lens being a positive lens made from a third material, said three lenses having "n" faces numbered 1–6, with "rn" being the radius of curvature of the nth face, and "tn" being the spacing nth and (n+1)st face;
at least one of said "r2" and/or "t4" being other than:

$|r2|<|F|;$ $|t4|>|0.05F|;$ and at least one of said "r4" and/or "r5" optionally being other than:

$|r4|>|2.5F|$ $|r5|>|0.5F|.$

11. A broadband ellipsometer as in claim 7, in which at least one of said at least two lenses is mounted in other than a manner specifically designed for minimizing stress thereon to minimize stress induced birefringence in said multi-element lens.

12. A broadband ellipsometer as in claim 7, in which at least one of said at least two lenses is mounted in other than a manner specifically designed for minimizing stress thereon to minimize stress induced birefringence in said at least one lens.

13. A broadband ellipsometer as in claim 7, in which the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved, and wherein cement is entered through holes in the wall of said tube which are near edges of said at least two lenses, to secure the positions of said lenses.

14. A method of improving the operation of a broadband ellipsometer or polarimeter for evaluating the characteristics of a sample comprising:
  a) providing broadband ellipsometer or polarimeter which comprises:
    broadband light source means for generating a polychromatic probe beam, said polychromatic probe beam comprising at least UV and Visible wavelengths;
    an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises holes through the wall thereof for accepting cement;
  b) effecting the relative position between at least two of said at least two lenses in said tube by, while actively monitoring of the effect of said at least two lenses on a beam of electromagnetic radiation caused to pass therethrough, adjusting said relative position until an acceptable effect is achieved on said electromagnetic beam, and wherein cement is entered through holes in the wall of said tube which are near edges of said at least two lenses, to secure the positions of said lenses;
such that said at least two lenses are precisely secured in said tube at desired locations relative to one another.

15. A method as in claim 14, in which there are three lenses present in said tube, each thereof being precisely located with respect to one another and secured in said position by cement which is entered into said holes through the wall of said tube when an acceptable effect on said beam of electromagnetic radiation is achieved.

16. A method as in claim 15, in which the three lenses which are precisely positioned with respect to one another are two calcium flouride lenses disposed on opposite sides of a fused silica lens.

17. A broadband ellipsometer or polarimeter for evaluating the characteristics of a sample comprising:
  a broadband light source for generating a polychromatic probe beam, said polychromatic probe beam comprising at least UV and Visible wavelengths, an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium flouride and fused silica, said lenses being present in a tube which comprises holes through the wall thereof for accepting cement;
such that lenses are placed in said tube at the location of said holes for accepting cement and cement is entered thereinto and allowed to dry, thereby securing said lenses in place;
said broadband ellipsometer or polarimeter system further comprising an analyzer system for monitoring a portion of a probe beam reflected from said sample and generating output signals responsive thereto, and a processor for evaluating characteristics of the sample based on the output signals;
said broadband ellipsometer or polarimeter being distinguished in that the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved on said beam of electromagnetic radiation, and wherein cement is entered through holes in the wall of said tube which are near edges of said at least two lenses, to secure the positions of said lenses.

18. A broadband ellipsometer or polarimeter as in claim 17, in which there are three lenses present and in which the relative position between the first and second, and/or between the second and third is precisely controlled prior to cementing them into position in said tube.

19. A broadband ellipsometer or polarimeter as in claim 18, in which there are three lenses having a combined focal length (F), the first lens being a positive lens made from a first material, the second lens being a negative lens made from a second material, and the third lens being a positive lens made from a third material, said three lenses having "n" faces numbered 1–6, with "rn" being the radius of curvature of the nth face, and "tn" being the spacing nth and (n+1)st face;
at least one of said "r2" and/or "t4" being other than:

$$|r2|<|F|;$$

$$|t4|>|0.05F|;$$

and at least one of said "r4" and/or "r5" optionally being other than:

$$|r4|>|2.5F|$$

$$|r5|>|0.5F|.$$

20. A broadband ellipsometer or polarimeter as in claim 18, in which the sequence of lenses is characterized by a selection for the group:
  (Converging(C))(Diverging(D))(Converging(C));
  (Converging(C))(Converging(C))(Diverging(D));
  (Diverging(D))(Diverging(D))(Converging(C));
  (Converging(C))(Diverging(D))(Diverging(D));
  (Diverging(D))(Converging(C))(Diverging(D));
  (Converging(C))(Converging(C))(Diverging(D))(Diverging(D));
  (Diverging(D))(Diverging(D))(Converging(C))(Converging(C));
  ((Diverging(D))(Converging(C))(Converging(C))(Diverging(D));
  (Converging(C))(Diverging(D))(Converging(C))(Diverging(D));
  (Converging(C))(Diverging(D))(Diverging(D))(Converging(C)); and
  (Diverging(D))(Converging(C))(Diverging(D))(Converging(C)).

21. A broadband ellipsometer or polarimeter as in claim 17, in which the sequence of lenses is characterized by a selection for the group:
  (Converging(C))(Diverging(D))(Converging(C));
  (Converging(C))(Converging(C))(Diverging(D));
  (Diverging(D))(Diverging(D))(Converging(C));
  (Converging(C))(Diverging(D))(Diverging(D));
  (Diverging(D))(Converging(C))(Diverging(D));
  (Converging(C))(Converging(C))(Diverging(D))(Diverging(D));
  (Diverging(D))(Diverging(D))(Converging(C))(Converging(C));

(Diverging(D))(Converging(C))(Converging(C))(Diverging(D));
(Converging(C))(Diverging(D))(Converging(C))(Diverging(D));
(Converging(C))(Diverging(D))(Diverging(D))(Converging(C)); and
(Diverging(D))(Converging(C))(Diverging(D))(Converging(C)).

22. An ellipsometer or polarimeter system comprising at least one multi-element lens placed at a selection from the group consisting of:
    at the input; and
    at the output;
said at least one multi-element lens being comprised of at least two elements which are made of different materials, such that in use the focal length for each wavelength in a range of wavelengths is essentially the same for every other wavelength is said range of wavelengths, at least one of said elements being firmly secured to the inner wall of a tube by securing means;
said ellipsometer or polarimeter system further comprising a broadband source for generating a polychromatic probe beam and a polarizer prior to a sample, and an analyzer and detector after said sample; and said polarimeter further having at least one compensator present at, at least one location selected from the group consisting of:
    before said sample; and
    after said samples
said ellipsometer or polarimeter being further characterized in that there are at least three lenses elements having a combined focal length (F), the first lens element being a positive lens made from a first material, the second lens element being a negative lens made from a second material, and the third lens element being a positive lens made from a third material, said three lenses having "n" faces numbered 1–6, with "rn" being the radius of curvature of the nth face, and "tn" being the spacing nth and (n+1)st face;
at least one of said "r2" and/or "t4" being other than:

$$|r2|<|F|;$$

$$|t4|>|0.05F|;$$

and at least one of said "r4" and/or "r5" optionally being other than:

$$|r4|>|2.5F|$$

$$|r5|>|0.5F|.$$

23. A broadband ellipsometer or polarimeter as in claim 22, in which the sequence of lenses is characterized by a selection for the group:
    (Converging(C))(Diverging(D))(Converging(C));
    (Converging(C))(Converging(C))(Diverging(D));
    (Diverging(D))(Diverging(D))(Converging(C));
    (Converging(C))(Diverging(D))(Diverging(D));
    (Diverging(D))(Converging(C))(Diverging(D));
    (Converging(C))(Converging(C))(Diverging(D))(Diverging(D));
    (Diverging(D))(Diverging(D))(Converging(C))(Converging(C));
    (Diverging(D))(Converging(C))(Converging(C))(Diverging(D));
    (Converging(C))(Diverging(D))(Converging(C))(Diverging(D));
    (Converging(C))(Diverging(D))(Diverging(D))(Converging(C)); and
    (Diverging(D))(Converging(C))(Diverging(D))(Converging(C)).

* * * * *